United States Patent
Watakabe et al.

(10) Patent No.: US 7,799,468 B2
(45) Date of Patent: Sep. 21, 2010

(54) ELECTROLYTE MATERIAL FOR POLYMER ELECTROLYTE FUEL CELLS, ELECTROLYTE MEMBRANE AND MEMBRANE-ELECTRODE ASSEMBLY

(75) Inventors: Atsushi Watakabe, Yokohama (JP); Satoru Hommura, Yokohama (JP); Seigo Kotera, Yokohama (JP); Susumu Saito, Yokohama (JP); Koichi Murata, Yokohama (JP); Masanori Sawaguchi, Yokohama (JP); Taiki Hoshino, Yokohama (JP); Junichi Tayanagi, Yokohama (JP); Eiji Endoh, Yokohama (JP)

(73) Assignee: Asahi Glass Company, Limited, Tokyo (JP)

( * ) Notice: Subject to any disclaimer, the term of this patent is extended or adjusted under 35 U.S.C. 154(b) by 1308 days.

(21) Appl. No.: 11/311,560

(22) Filed: Dec. 20, 2005

(65) Prior Publication Data

US 2006/0099476 A1    May 11, 2006

Related U.S. Application Data

(63) Continuation of application No. PCT/JP2005/006625, filed on Apr. 4, 2005.

(30) Foreign Application Priority Data

| Apr. 2, 2004 | (JP) | 2004-109869 |
| Oct. 26, 2004 | (JP) | 2004-311191 |
| Nov. 2, 2004 | (JP) | 2004-319086 |

(51) Int. Cl.
*H01M 6/18* (2006.01)

(52) U.S. Cl. .......... 429/314; 429/33; 429/317; 429/188; 252/62.2; 521/25; 521/27

(58) Field of Classification Search .......... 429/33, 429/314, 317, 188; 252/62.2; 521/25, 27
See application file for complete search history.

(56) References Cited

U.S. PATENT DOCUMENTS

| 4,810,806 | A | 3/1989 | Krespan |
| 4,973,714 | A | 11/1990 | Krespan |
| 6,610,789 | B2 | 8/2003 | Watakabe et al. |
| 7,271,229 | B2 * | 9/2007 | Okazoe et al. ............ 526/247 |
| 7,429,428 | B2 * | 9/2008 | Watakabe .................... 429/33 |
| 2002/0142207 | A1 | 10/2002 | Watakabe et al. |
| 2003/0198854 | A1 | 10/2003 | Watakabe et al. |
| 2004/0230018 | A1 | 11/2004 | Okazoe et al. |
| 2005/0037265 | A1 | 2/2005 | Watakabe |
| 2005/0266291 | A1 | 12/2005 | Watakabe |
| 2006/0029854 | A1 | 2/2006 | Watakabe et al. |

FOREIGN PATENT DOCUMENTS

| EP | 1126537 | 8/2001 |
| JP | 64-79170 | 3/1989 |
| JP | 5-213929 | 8/1993 |
| JP | 2002-260705 | 9/2002 |
| WO | WO 00/56694 | 9/2000 |
| WO | WO 03/037885 | 5/2003 |
| WO | 2004/066426 | 8/2004 |
| WO | WO 2004/097851 | * 11/2004 |

OTHER PUBLICATIONS

U.S. Appl. No. 11/618,088, filed Dec. 29, 2006, Watakabe, et al.
U.S. Appl. No. 11/624,499, filed Jan. 18, 2007, Tayanagi, et al.
U.S. Appl. No. 11/271,915, filed Nov. 14, 2005, Kasahara, et al.
U.S. Appl. No. 12/042,810, filed Mar. 5, 2008, Tayanagi, et al.
U.S. Appl. No. 11/741,008, filed Apr. 27, 2007, Hommura, et al.
U.S. Appl. No. 12/535,709, filed Aug. 5, 2009, Watakabe.
U.S. Appl. No. 11/183,748, filed Jul. 19, 2005, Tayanagi, et al.

* cited by examiner

*Primary Examiner*—Laura S Weiner
(74) *Attorney, Agent, or Firm*—Oblon, Spivak, McClelland, Maier & Neustadt, L.L.P.

(57) ABSTRACT

An electrolyte material for polymer electrolyte fuel cells, which is made of a polymer containing repeating units based on a fluoromonomer having a radical polymerization reactivity, wherein the repeating units contain a 5-membered ring (which may contain 1 or 2 oxygen atoms), of which at least one carbon atom is contained in the main chain of the polymer, and an ionic group such as a sulfonic acid group which is bonded to the 5-membered ring directly or via a perfluoroalkylene group having a linear or branched structure; and the polymer has a softening temperature of at least 120° C.

38 Claims, 2 Drawing Sheets

ELECTROLYTE MATERIAL FOR POLYMER ELECTROLYTE FUEL CELLS, ELECTROLYTE MEMBRANE AND MEMBRANE-ELECTRODE ASSEMBLY

TECHNICAL FIELD

The present invention relates to an electrolyte material constituting an electrolyte membrane, or an electrolyte material contained in a catalyst layer for polymer electrolyte fuel cells. Particularly, it relates to an electrolyte material which is made of a polymer having a high softening temperature and high mechanical strength and which makes an operation of fuel cells at a high temperature possible. Further, it relates to a fluoropolymer and a fluoromonomer useful as a raw material for such an electrolyte material.

BACKGROUND ART

Heretofore, for membranes for electrolysis of sodium chloride, for membranes or catalyst layers for polymer electrolyte fuel cells, it has been common to employ a polymer which is obtainable by hydrolyzing a copolymer of a fluoromonomer represented by the formula $CF_2=CF-(OCF_2CFR^x)_{x1}-O_{x2}-(CF_2)_{x3}-SO_2F$ (wherein $R^x$ is fluorine atom or a trifluoromethyl group, x1 is an integer of from 0 to 3, x2 is 0 or 1, and x3 is an integer of from 1 to 12, provided that x1+x2>0) with tetrafluoroethylene, or a polymer having sulfonic acid groups obtainable by further converting it to an acid form (hereinafter referred to as a sulfonic acid polymer).

Such a sulfonic acid polymer has a softening temperature in the vicinity of 80° C. Accordingly, the operation temperature of a fuel cell employing such a polymer is usually at most 80° C. However, in a case where hydrogen obtainable by reforming an organic compound such as methanol, natural gas or gasoline, is used as a fuel gas for a fuel cell, if carbon monoxide is contained even in a trace amount, the electrode catalysts will be poisoned, and the output of the fuel cell tends to be low. Accordingly, in order to prevent such a trouble, it is desired to increase the operation temperature. Further, also with a view to downsizing the cooling device for fuel cells, it is desired to increase the operation temperature, and preferably, a membrane for operation at a temperature of at least 120° C. is desired. However, the above-mentioned conventional sulfonic acid polymer has a low softening temperature and can not satisfy such demands. As a polymer having a high softening temperature, a copolymer of a monomer represented by the following formula (y) (hereinafter referred to simply as a monomer (y)) with tetrafluoroethylene, has been proposed (Patent Document 1). In the formula, $Q^y$ is a fluorinated bivalent organic group, and each of $R^{y1}$ to $R^{y3}$ which are independent of one another, is a fluorine atom or a fluorinated monovalent organic group.

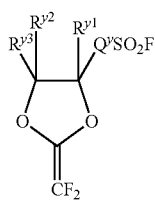
(y)

Further, Patent Document 2 discloses a monomer represented by the following formula (z) (hereinafter referred to as a monomer (z)). Here, $X^z$ represents a various functional group such as F, Cl, $-OC_6F_5$, $-CN$, $-COF$, $-COOR^{z1}$ (wherein $R^{z1}$ is $-CH_3$, $-C_2H_5$ or $CH_2CF_3$), $-SO_2F$ or $-SO_2Cl$, $R^z$ is a fluorine atom or a perfluoroalkyl group, and $Q^z$ is a perfluoroalkylene group which may contain an etheric oxygen atom.

(z)

However, with respect to a monomer (z) wherein $X^z$ is $-SO_2F$ or $SO_2Cl$, no synthetic example is disclosed, and there is no indication to use a polymer obtained by polymerizing the monomer (z) for fuel cells.

Patent Document 1: WO03/037885
Patent Document 2: U.S. Pat. No. 4,973,714

DISCLOSURE OF THE INVENTION

Object to be Accomplished by the Invention

As mentioned above, fuel cells are preferably used under a high temperature condition. For example, polymer electrolyte fuel cells are preferably operated at a high temperature (for example, at a temperature of at least 120° C.) in order to facilitate heat removal and to increase the efficiency for power generation. For this purpose, a sulfonic acid polymer showing high mechanical strength in a high temperature region, is desired for e.g. the electrolyte membrane for polymer electrolyte fuel cells.

However, in a case where $Q^y$ in the monomer (y) in Patent Document 1 is a perfluoro(etheric oxygen atom-containing alkylene) group such as $-CF_2OCF_2CF_2-$, the softening temperature of the polymer obtainable by polymerizing the monomer (y) was not sufficiently high. Further, if the carbon number of $Q^y$ in the monomer (y) becomes large, the softening temperature of the polymer obtainable by polymerizing the monomer (y) is considered to become low.

Accordingly, it is an object of the present invention to provide an electrolyte material for polymer electrolyte fuel cells, which is made of a polymer which has a high softening temperature and whereby the mechanical strength can be maintained even when used under a high temperature condition.

Means to Accomplish Object

The present invention provides an electrolyte material for polymer electrolyte fuel cells, which is made of a polymer containing repeating units based on a fluoromonomer having a radical polymerization reactivity, wherein the repeating units contain a 5-membered ring (which may contain 1 or 2 oxygen atoms), of which at least one carbon atom is contained in the main chain of the polymer, and an ionic group which is bonded to the 5-membered ring directly or via a perfluoroalkylene group having a linear or branched structure; the ionic group is represented by the formula $-(SO_2X(SO_2R^f)_g)^-H^+$, wherein $R^f$ is a linear or branched perfluoroalkyl group which may contain an etheric oxygen atom, and X is an oxygen atom, a nitrogen atom or a carbon atom, provided that when X is an oxygen atom, g=0, when X is a nitrogen atom, g=1, and when X is a carbon atom, g=2, and the polymer has a softening temperature of at least 120° C.; and an electrolyte membrane for polymer electrolyte fuel cells, made of such an electrolyte material.

The above ionic group (hereinafter referred to as the present ionic group) is a strongly acidic group such as a sulfonic acid group, which is suitable as an ionic group for an electrolyte material for fuel cells. The repeating units based on an alicyclic fluoromonomer, being repeating units of this polymer, may contain two or more such present ionic groups.

Further, the present invention provides a process for producing an electrolyte material for polymer electrolyte fuel cells, which is a process for producing the above-described electrolyte material and which comprises subjecting a fluoromonomer having a 5-membered ring which may have 1 or 2 oxygen atoms, a carbon-carbon double bond, of which at least one of the carbon atoms is included in the 5-membered ring, and a fluorosulfonyl group which is bonded to the 5-membered ring directly or via a perfluoroalkylene group having a linear or branched structure, to radical polymerization in the presence of a radical initiating source, and then converting the fluorosulfonyl group to an ionic group represented by the formula $-(SO_2X(SO_2R^f)_g)^-H^+$, wherein $R^f$ is a linear or branched perfluoroalkyl group which may contain an etheric oxygen atom, and X is an oxygen atom, a nitrogen atom or a carbon atom, provided that when X is an oxygen atom, $g=0$, when X is a nitrogen atom, $g=1$, and when X is a carbon atom, $g=2$.

Further, the present invention provides a membrane-electrode assembly for polymer electrolyte fuel cells, which comprises a cathode and an anode each having a catalyst layer containing a catalyst and a polymer electrolyte, and a polymer electrolyte membrane interposed between the cathode and the anode, wherein the polymer electrolyte membrane is made of the above-described polymer electrolyte material.

Further, the present invention provides a membrane-electrode assembly for polymer electrolyte fuel cells, which comprises a cathode and an anode each having a catalyst layer containing a catalyst and a polymer electrolyte, and a polymer electrolyte membrane interposed between the cathode and the anode, wherein the polymer electrolyte contained in at least one of the catalyst layers of the cathode and the anode, is the above-described electrolyte material.

Furthermore, the present invention provides a polymer containing monomer units represented by the following formula (M), and a polymer containing monomer units represented by the following formula (P), which are useful as the above-described electrolyte material:

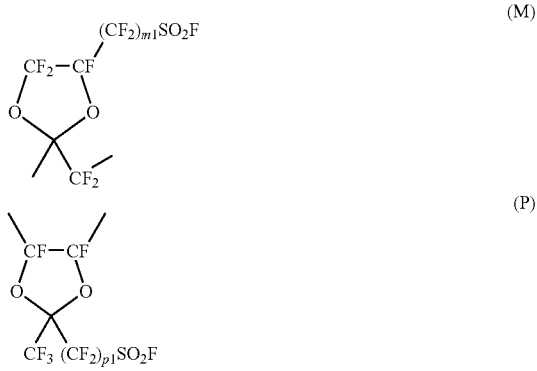

wherein each of m1 and p1 which are independent of each other, is an integer of from 1 to 6.

Further, the present invention provides a compound represented by the following formula (m) and a compound represented by the following formula (p):

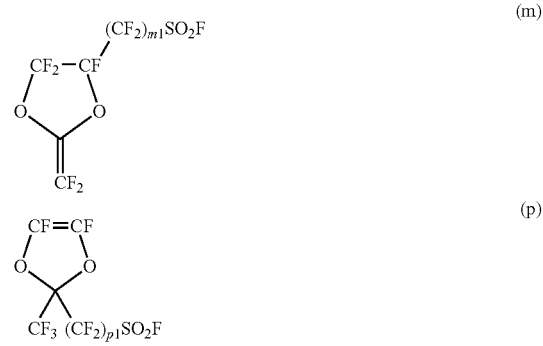

wherein each of m1 and p1 which are independent of each other, is an integer of from 1 to 6.

Effects of the Invention

According to the present invention, it is possible to provide an electrolyte material which has a softening temperature higher than the conventional perfluorosulfonic acid polymer, and it is thereby possible to obtain a polymer electrolyte fuel cell which can be operated at a temperature higher than before.

BEST MODE FOR CARRYING OUT THE INVENTION

Figure 1:
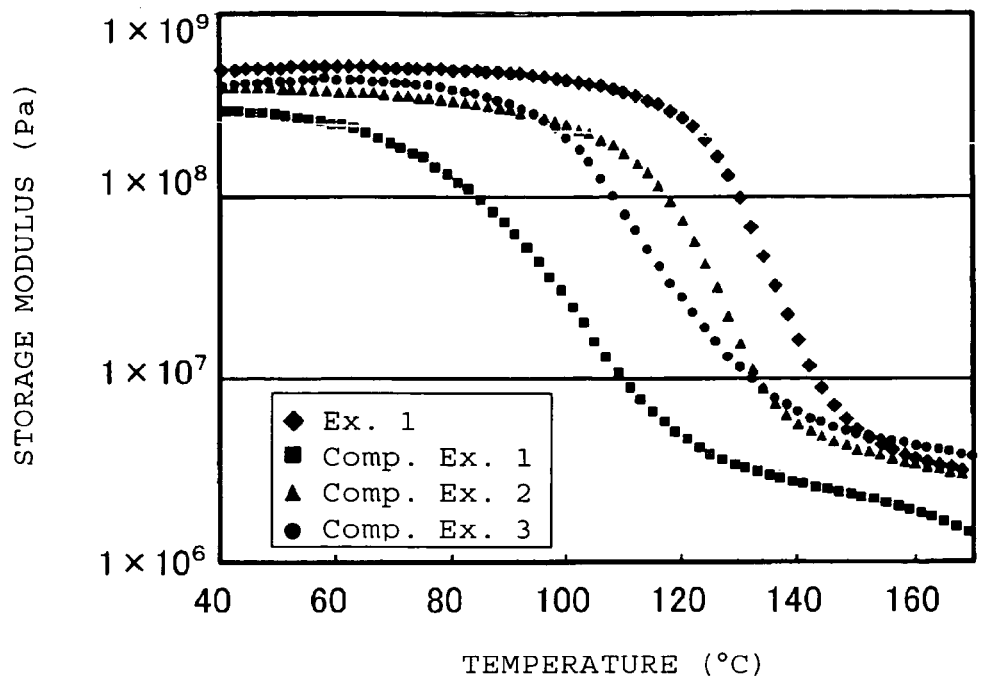
FIG. 1 is a graph showing the temperature dependency of the storage modulus with respect to the electrolyte materials in Example 1 and Comparative Examples 1 to 3.
Figure 2:
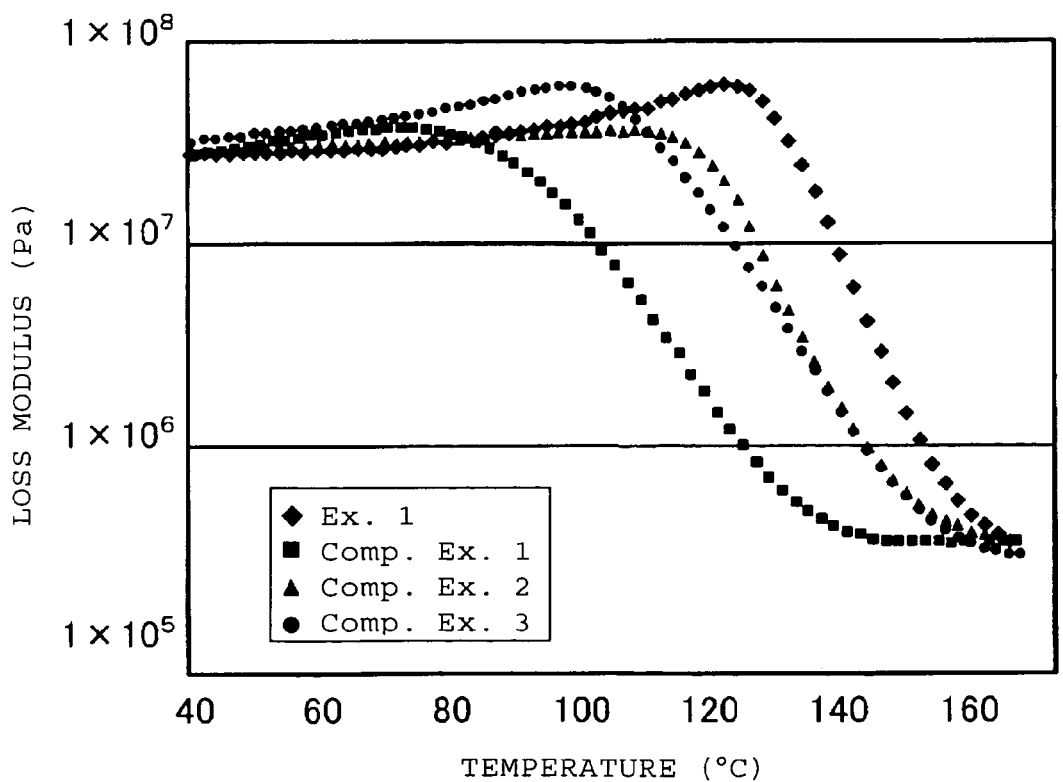
FIG. 2 is a graph showing the temperature dependency of the loss modulus with respect to the electrolyte materials in Example 1 and Comparative Examples 1 to 3.

In this specification, a compound represented by the formula (a) will be referred to as a compound (a). Units represented by the formula (A) will be referred to as units (A). A polymer containing units (A) will be referred to as a polymer (A). The same applies to compounds, units and polymers represented by other formulae.

Units in a polymer are meant for monomer units (also referred to as repeating units) derived from a monomer and formed by polymerization of such a monomer. In the present invention, the units may be units directly formed by a polymerization reaction or units formed by a chemical conversion after the polymerization reaction.

In this specification, an organic group means a group containing at least one carbon atom. The organic group may, for example, be a hydrocarbon group, a halogenated hydrocarbon group, a heteroatom-containing hydrocarbon group or a halogenated (heteroatom-containing hydrocarbon) group. The hydrocarbon group means a group comprising carbon atoms and hydrogen atoms. Further, the halogenated hydrocarbon group means a group having at least one hydrogen atom bonded to a carbon atom substituted by a halogen atom. The heteroatom-containing hydrocarbon group means a hydrocarbon group containing a heteroatom (an oxygen atom, a nitrogen atom, a sulfur atom or the like) and/or a heteroatomic group (—C—C(=O)—C—, —C—SO$_2$—C—, or the like). Further, the halogenated (heteroatom-containing hydrocarbon) group means a group wherein at least one hydrogen atom bonded to a carbon atom in the above heteroatom-containing hydrocarbon group, substituted by a halogen atom.

The polymer constituting the electrolyte material for solid electrolyte fuel cells of the present invention (hereinafter referred to as the present electrolyte material) contains repeating units based on a fluoromonomer having a radical polymerization reactivity.

Such repeating units contain repeating units (hereinafter referred to as the present alicyclic units) which contain a 5-membered ring (which may contain 1 or 2 oxygen atoms), of which at least one carbon atom is contained in the main chain of the polymer, and an ionic group which is bonded to the 5-membered ring directly or via a perfluoroalkylene group having a linear or branched structure.

The carbon chain length of the above perfluoroalkylene group is preferably from 1 to 6, particularly preferably from 2 to 4.

The above ionic group is represented by the formula —(SO$_2$X(SO$_2$R$^f$)$_g$)$^-$H$^+$ (wherein R$^f$, X and g are as defined above, and the same applies hereinafter).

Specifically, the ionic group is preferably a —SO$_3^-$H$^+$ group such as a sulfonic acid group, a sulfonimide group (—SO$_2$NSO$_2$R$^f$)$^-$H$^+$ or a sulfone methide group (—SO$_2$C(SO$_2$R$^f$)$_2$)$^-$H$^+$. Here, the carbon number of R$^f$ is preferably from 1 to 8, particularly preferably from 1 to 6. Specifically, a perfluoromethyl group or a perfluoroethyl group is, for example, preferred. In a case of a sulfone methide group, two R$^f$ may be the same or different.

As such a polymer, a polymer containing the following units (A) or a polymer containing the following units (B) is preferred;

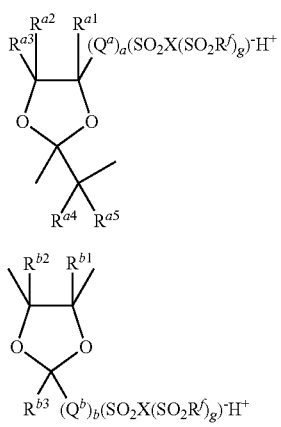

wherein Q$^a$ is a perfluoroalkylene group having a linear or branched structure, each of R$^{a1}$ to R$^{a5}$ which are independent of one another, is a perfluoroalkyl group or a fluorine atom, and a is 0 or 1 (the same applies hereinafter). Q$^b$ is a perfluoroalkylene group having a linear or branched structure, each of R$^{b1}$ to R$^{b3}$ which are independent of one another, is a perfluoroalkyl group or a fluorine atom, and b is 0 or 1 (the same applies hereinafter).

In the units (A), particularly for high polymerizability, at least one of R$^{a4}$ and R$^{a5}$ is preferably a fluorine atom. It is particularly preferred that each of R$^{a4}$ and R$^{a5}$ is a fluorine atom. Further, it is preferred that also each of R$^{a1}$ to R$^{a3}$ is a fluorine atom. Further, the carbon chain length of Q$^a$ is preferably from 1 to 6, particularly preferably from 2 to 4. Specifically, the following units (A1) are preferred. Here, a1 is from 0 to 6, preferably from 2 to 4.

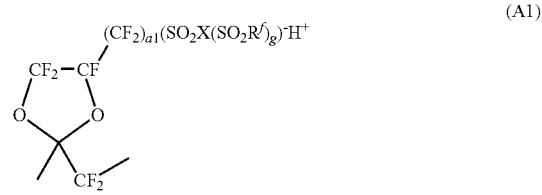

In units (B), at least one of R$^{b1}$ and R$^{b2}$ is preferably a fluorine atom. It is particularly preferred that each of R$^{b1}$ and R$^{b2}$ is a fluorine atom. R$^{b3}$ is preferably a trifluoromethyl group. Further, the carbon chain length of Q$^b$ is preferably from 1 to 6, particularly preferably from 2 to 4. Specifically, the following units (B1) are preferred. Here, b1 is from 1 to 6, preferably from 2 to 4.

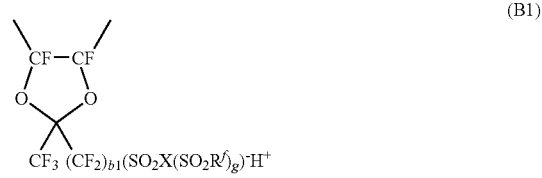

Further, in addition to units (A) and units (B), the following units (C) to (E) are also preferred as the present alicyclic units;

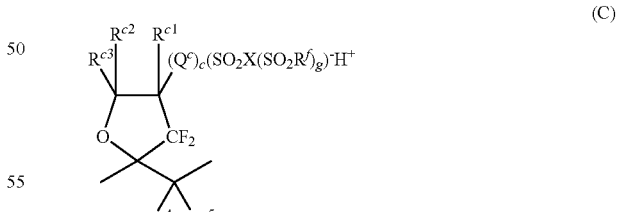

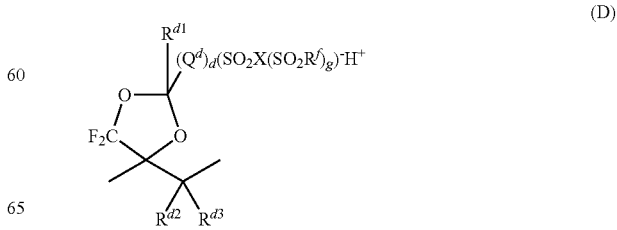

-continued

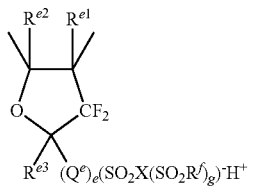
(E)

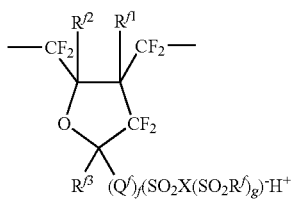
(F)

wherein each of $Q^c$, $Q^d$, $Q^e$ and $Q^f$ which are independent of one another, is a perfluoroalkylene group having a linear or branched structure, and its carbon chain length is preferably from 1 to 6 (the same applies hereinafter). Each of c, d, e and f which are independent of one another, is 0 or 1 (the same applies hereinafter). Each of $R^{c1}$ to $R^{c5}$, $R^{d1}$ to $R^{d3}$, $R^{e1}$ to $R^{e3}$ and $R^{f1}$ to $R^{f3}$ which are independent of one another, is a perfluoroalkyl group or a fluorine atom (the same applies hereinafter). Each of $R^{c1}$ to $R^{c5}$, $R^{d2}$, $R^{d3}$, $R^{e1}$, $R^{e2}$ and $R^{f1}$ to $R^{f3}$ is preferably a fluorine atom.

The polymer constituting the present electrolyte material (hereinafter sometimes referred to simply as the present polymer) may be a homopolymer or a copolymer of the present alicyclic units with one or more other units. Here, other units mean units other than the present alicyclic units.

For example, when the present polymer is made of a polymer (A), the polymer (A) here may be a polymer comprising at least one type of units (A), or a polymer comprising at least one type of units (A) and at least one type of units other than units (A). As the latter polymer (A), preferred is a polymer comprising one type of units (A) and at least one type of units other than units (A).

Further, when the present polymer is made of a polymer (B), the polymer (B) here may be a polymer comprising at least one type of units (B), or a polymer comprising at least one type of units (B) and at least one type of units other than units (B). As the latter polymer (B), preferred is a polymer comprising one type of units (B) and at least one type of units other than units (B).

Further, in a case where the polymer containing the present alicyclic units is a copolymer containing at least two types of units, the arrangement of the respective units may be a block-form, a graft-form or a random-form. Among them, from the viewpoint of efficiency in the production of the present electrolyte material, the arrangement of the respective units is preferably a random-form. Further, such a polymer may be cross-linked.

As such other units, units having the following compound (w1), the following compound (w2) or the following compound (w3) polymerized, are preferred;

$CHR^{11}=CR^{12}R^{13}$ (w1)

$CFR^{14}=CR^{15}R^{16}$ (w2)

$CR^{17}R^{18}=CR^{19}-Q^1-CR^{20}=CF_2$ (w3)

wherein each of $R^{11}$, $R^{12}$ and $R^{13}$ which are independent of one another, is a hydrogen atom, a fluorine atom or a monovalent fluorinated saturated organic group. Each of $R^{14}$, $R^{15}$ and $R^{16}$ which are independent of one another, is a fluorine atom, a chlorine atom or a monovalent fluorinated saturated organic group which may contain an etheric oxygen atom. Or, two groups selected from $R^{14}$, $R^{15}$ and $R^{16}$ may together form a bivalent fluorinated organic group, while the remaining one group is a fluorine atom or a monovalent fluorinated saturated organic group. Each of $R^{17}$, $R^{18}$, $R^{19}$ and $R^{20}$ which are independent of one another, is a hydrogen atom, a fluorine atom or a monovalent fluorinated organic group, and $Q^1$ is a bivalent fluorinated organic group.

Specific examples of the compound (w1) include $CHF=CF_2$, $CH_2=CF_2$, $CH_2=CHF$, $CH_2=CH_2$, $CH_2=CHCH_3$, $CH_2=CH(CF_2)_4F$, and $CH_2=CHCH_2(CF_2)_8F$.

Specific examples of the compound (w2) include $CF_2=CF_2$, $CFCl=CF_2$, $CF_2=CFCF_3$, the following compound (w2-1), the following compound (w2-2) and the following compound (w2-3), and $CF_2=CFCF_2OCF_3$.

Here, t is an integer of from 0 to 3, $R^{t1}$ is a fluorine atom or a trifluoromethyl group, and $R^{t2}$ is a $C_{1-12}$ perfluoroalkyl group. Further, $R^{t2}$ may have a liner structure or a branched structure. Each of $R^{t3}$ and $R^{t4}$ which are independent of each other, is a fluorine atom or a $C_{1-3}$ perfluoroalkyl group, and $R^{t5}$ is a fluorine atom or a trifluoromethoxy group. Each of $R^{t6}$ and $R^{t7}$ which are independent of each other, is a fluorine atom or a $C_{1-7}$ perfluoroalkyl group.

$CF_2=CF-(-OCF_2CFR^{t1}-)_t-OR^{t2}$ (w2-1)

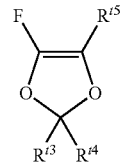
(w2-2)

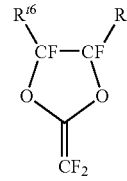
(w2-3)

Specific examples of the compound (w3) include $CF_2=CFOCF_2CF_2CF=CF_2$, $CF_2=CFOCF(CF_3)CF_2CF=CF_2$ and $CF_2=CFOCF_2CF=CF_2$.

In the present polymer, from the viewpoint of the durability, such other units preferably contain substantially no hydrogen atoms. As the units containing substantially no hydrogen atoms, preferred are units obtained by polymerizing the compound (w2) wherein each of $R^{14}$, $R^{15}$ and $R^{16}$ is a fluorine atom or a perfluoroorganic group or a compound (w3) wherein each of $R^{17}$, $R^{18}$, $R^{19}$ and $R^{20}$ is a fluorine atom, and $Q^1$ is a perfluoroalkylene group which may contain an etheric oxygen atom. Further, it is particularly preferred to contain, as such other units, units having $CF_2=CF_2$ polymerized, or units having $CF_2=CF_2$ polymerized and units having a perfluoro(2,2-dimethyl-1,3-dioxole) as one type of the compound (w2-2) polymerized, since such a polymer will have a sufficient strength and a high softening temperature when formed into a membrane.

The proportion of the present alicyclic units to the total units in the present polymer may suitably be selected as the case requires. In a case where the present polymer is made of a non-crosslinked random copolymer, the proportion of the present alicyclic units is preferably at least 5 mol %, particularly preferably at least 10 mol %, from such a viewpoint that a high power generation efficiency can be obtained with a low resistance. Further, from the viewpoint of the mechanical properties, the proportion of the present alicyclic units is preferably at most 50 mol %, more preferably at most 35 mol %, particularly preferably at most 30 mol %. Further, in a case where the present polymer is a graft polymer or a block polymer, the proportion of the present alicyclic units in the entire polymer is preferably within the above range. In the graft polymer or the block polymer, the segments containing the present alicyclic units may be those composed solely of the present alicyclic units.

In a case where the present polymer is made of a crosslinked polymer, the proportion of the present alicyclic units is preferably at least 5 mol %, more preferably at least 10 mol %, particularly preferably at least 15 mol %, from such a viewpoint that a high power generation efficiency can be obtained with a low resistance in the same manner as in the case where the polymer is not crosslinked. With a view to improving the mechanical properties with maintaining the ion exchange capacity to be high, the proportion of the present alicyclic units to the total units in the present polymer, is preferably at most 95 mol %, more preferably at most 75 mol %, particularly preferably at most 50%.

The ion exchange capacity (hereinafter referred to as AR) of the present electrolyte material is preferably from 0.5 to 3.0 meq/g dry resin (hereinafter referred to as meq/g). If $A_R$ of the electrolyte material is too small, the water content of the electrolyte material tends to be low, whereby the ion conductivity tends to be low, and when it is used as an electrolyte membrane for a polymer electrolyte fuel cell, it tends to be difficult to obtain a sufficient cell output. From the same viewpoint, it is more preferably at least 0.7 meq/g, further preferably at least 0.9 meq/g. On the other hand, if $A_R$ becomes too large, the density of ion exchange groups in the electrolyte material increases, and the strength of the polymer electrolyte material tends to be low. From the same viewpoint, $A_R$ of the present electrolyte material is further preferably at most 2.0 meq/g.

Further, for the present electrolyte material to have sufficient strength particularly for use as a membrane material for fuel cells, $\Delta T$ as defined below, is preferably at least 40° C., more preferably at least 60° C. From the viewpoint of the strength of the polymer, there is no upper limit for $\Delta T$. However, in a case where the membrane is formed by a casting method, or the electrolyte material is to be incorporated in a catalyst layer, from the viewpoint of the solubility or dispersibility in a solvent, or in a case where it is melt-molded, from the viewpoint of the melt moldability of the precursor for the electrolyte material, $\Delta T$ is preferably at most 150° C., more preferably at most 120° C.

$\Delta T$ is defined by the following formula by using the data obtained by measurement of the dynamic viscoelasticity.

$$\Delta T = T_2 - T_1,$$

$T_2$: the temperature at which the storage modulus becomes $1 \times 10^6$ Pa, $T_1$: the peak temperature of the loss modulus (the softening temperature).

The above-described relation between the polymer strength and $\Delta T$ is considered to be attributable to the fact that $\Delta T$ increases as the molecular weight of the polymer increases. For the measurement of the dynamic viscoelasticity, the temperature is raised until the stock modulus decreases to $1 \times 10^6$ Pa. However, in a case where the molecular weight of the polymer is very large, there may be a case where the modulus will not decrease to $1 \times 10^6$ Pa till in the vicinity of 350° C. i.e. the decomposition temperature of the polymer. In such a case, $T_2 > T_{max}$, where $T_{max}$ is the maximum temperature for measurement. For example, in a case where $T_1 = 150°$ C. and $T_{max} = 340°$ C., $\Delta T > 190°$ C.

The present electrolyte material has a softening temperature of at least 120° C. In the case of a polymer containing units wherein an ionic group and a 5-membered ring are bonded via an etheric oxygen atom-containing perfluoroalkylene group, as specifically disclosed in Examples in WO03/37885, the softening temperature is about 100° C., and by the structure of the present alicyclic units, a softening temperature of at least 120° C. can be accomplished. If the softening temperature is high, it is possible to have a fuel cell operated at a high temperature. Here, the softening temperature in the present invention is defined to be a temperature at which a loss modulus shows the maximum value in the measurement of the dynamic viscoelasticity at a temperature raising rate of 2° C./min at a frequency of 1 Hz in a temperature range where the resin is softened and the storage modulus abruptly decreases. Namely, this softening temperature is the same as $T_1$ mentioned above.

In a process for producing the polymer constituting the present electrolyte material, a fluoromonomer having a 5-membered ring which may have 1 or 2 oxygen atoms, a carbon-carbon double bond, of which at least one carbon atom is contained in the above 5-membered ring, and a fluorosulfonyl group bonded to the above 5-membered ring directly or via a perfluoroalkylene group having a linear or branched structure, is subjected to radical polymerization in the presence of a radical initiating source.

For example, as a process for producing the polymer (A), a process by a polymerization reaction of a monomer may be mentioned. More specifically, a process may be mentioned wherein at least one type of the following compounds (A), or at least one type of such compounds and at least one type of compounds capable of forming other units, are polymerized. Further, a reaction to chemically convert other units to another structure, may be carried out. Such a polymerization process is not particularly limited, and may preferably carried out in accordance with the method disclosed in WO03/37885. As the compounds (a), the following compounds (a1) are preferred, and the after-mentioned compounds (m) are particularly preferred.

(a)

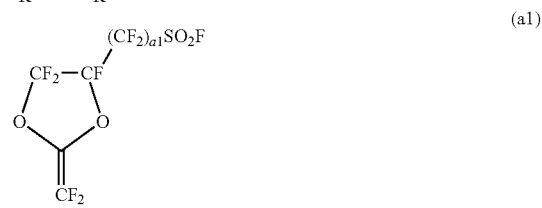

(a1)

Likewise, as a process for producing the polymer (B), at least one type of the following compounds (b), or at least one type of the compounds (b) and at least one type of compounds capable of forming other units, may be subjected to radical polymerization. As the compounds (b), the following compounds (b1) are preferred, and the after-mentioned compounds (p) are particularly preferred.

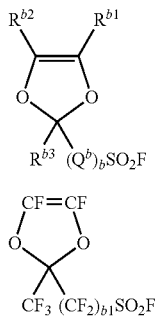

Further, in a process for producing the above-mentioned polymer containing units (C), the following compound (c) is subjected to radical polymerization. Likewise, the above-mentioned polymer containing units (D) may be produced by subjecting the following compound is (d) to radical polymerization, the above-mentioned polymer containing units (E) may be produced by subjecting the following compound (e) to radical polymerization, and the above-mentioned polymer containing units (F) may be produced by subjecting the following compound (f) to radical polymerization:

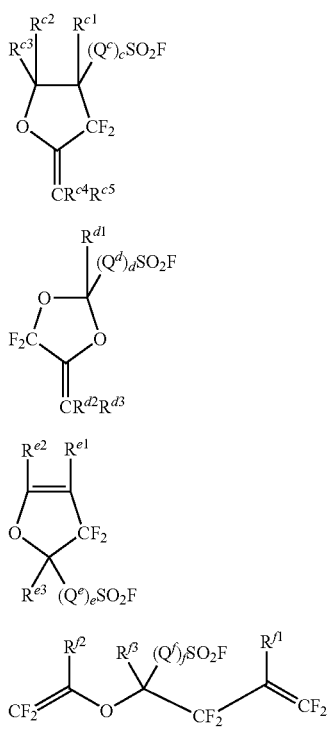

Such polymerization reactions are not particularly limited so long as they are carried out under such a condition that radicals will be formed. For example, they may be carried out by bulk polymerization, solution polymerization, suspension polymerization, emulsion polymerization, polymerization in a liquid or supercritical carbon dioxide, etc.

The method to let radicals form, is not particularly limited, and for example, a method of irradiating radiation rays such as ultraviolet rays, γ-rays or electron rays, may be employed, or a method of using a radical initiator which is commonly used in a radical polymerization, may be employed. The reaction temperatures for the polymerization reactions are not particularly limited, and for example, they are usually from about 15 to 150° C. In a case where a radical initiator is to be employed, the radical initiator may, for example, be a bis (fluoroacyl) peroxide, a bis(chlorofluoroacyl) peroxide, a dialkyl peroxy dicarbonate, a diacyl peroxide, a peroxyester, an azo compound or a persulfate.

In a case where solution polymerization is to be carried out, a solvent subject to little chain transfer to the solvent, is employed. And, a prescribed amount of one or more above-mentioned fluoromonomers is put into the solvent, and a radical initiator, etc. may be added to let radicals form thereby to carry out the polymerization. Gaseous monomers and liquid monomers may be added all at once, sequentially or continuously.

Here, the solvent which may be used, may, for example, be a perfluorotrialkylamine such as perfluorotributylamine, a perfluorocarbon such as perfluorohexane or perfluorooctane, a hydrofluorocarbon such as 1H,4H-perfluorobutane or 1H-perfluorohexane, or a chlorofluorocarbon such as 3,3-dichloro-1,1,1,2,2-pentafluoropropane or 1,3-dichloro-1,1,2,2,3-pentafluoropropane. To adjust the molecular weight, a hydrocarbon compound such as hexane or methanol may be added.

The suspension polymerization may be carried out by using water as a dispersing medium, adding a monomer to be polymerized, and employing, as a radical initiator, a nonionic initiator such as a bis(fluoroacyl) peroxide, a bis(chlorofluoroacyl) peroxide, a dialkyl peroxy dicarbonate, a diacyl peroxide, a peroxyester or an azo compound. A solvent mentioned with respect to the solution polymerization may be added as an adjuvant. Further, in order to prevent flocculation of suspended particles, a surfactant may optionally be added as a dispersion stabilizer.

The present polymer which is crosslinked, is preferably produced by polymerizing a fluoromonomer with a crosslinkable monomer. For example, a process for producing a crosslinked polymer (A) may be carried out by a method of polymerizing the compound (A) with a crosslinkable monomer.

The crosslinkable monomer may, for example, be the following compound (w4) or the following compound (w5) (wherein $Q^2$ is a single bond, an oxygen atom or a $C_{1-10}$ perfluoroalkylene group which may contain an etheric oxygen atom, and $Q^3$ is a $C_{1-10}$ perfluoroalkylene group which may contain an etheric oxygen atom).

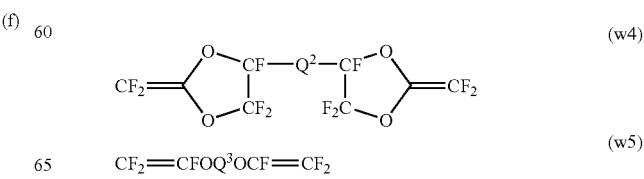

In the process for producing the present polymer, —SO$_2$F groups in the polymer obtained by radical polymerization of a fluoromonomer are converted to ionic groups represented by —(SO$_2$X(SO$_2$R$^f$)$_g$)$^-$H$^+$.

In a case where ionic groups are sulfonic acid groups, conversion from —SO$_2$F groups to sulfonic acid groups, can be carried out by a known method. For example, a method may be mentioned wherein after alkali hydrolysis treatment, acid treatment is further carried out to convert them to —SO$_3{}^{31}$H$^+$ groups. Such a method is preferably carried out in accordance with the method disclosed in WO03/37885.

For example, the polymer (A) as a polymer having other units, may be produced by a method of copolymerizing the compound (a) with another copolymerizable monomer, followed by treatment such as hydrolysis to convert —SO$_2$F groups to ionic groups. Likewise, the polymer (B) is preferably obtained by converting —SO$_2$F groups in a polymer obtained by radical polymerization of at least one type of the compound (b), to ionic groups by treatment such as hydrolysis.

For example, as a process for producing the polymer (A1), it is preferably obtained by converting —SO$_2$F groups to —(SO$_2$X(SO$_2$R$^f$)$_a$)$^-$H$^+$ groups after polymerizing the compound (a1)

Further, a —SO$_2$F group in a fluoromonomer or in a polymer obtained by radical polymerization of a fluoromonomer, can be converted to a sulfonimide group by a reaction with R$^f$SO$_2$NHM$^a$ (wherein M$^a$ is an alkali metal or a primary to quaternary ammonium, and the same applies hereinafter), a reaction with R$^f$SO$_2$NH$_2$ in the presence of an alkali metal hydroxide, an alkali metal carbonate, M$^a$F, ammonia or a primary to tertiary amine, or a reaction with R$^f$SO$_2$NM$^a$Si(CH$_3$)$_3$. In such reactions, the sulfonimide group will be obtained in a salt form derived from the base used.

For example, a reaction scheme wherein the compound (a1) is employed, will be shown below. J is Cl or Br.

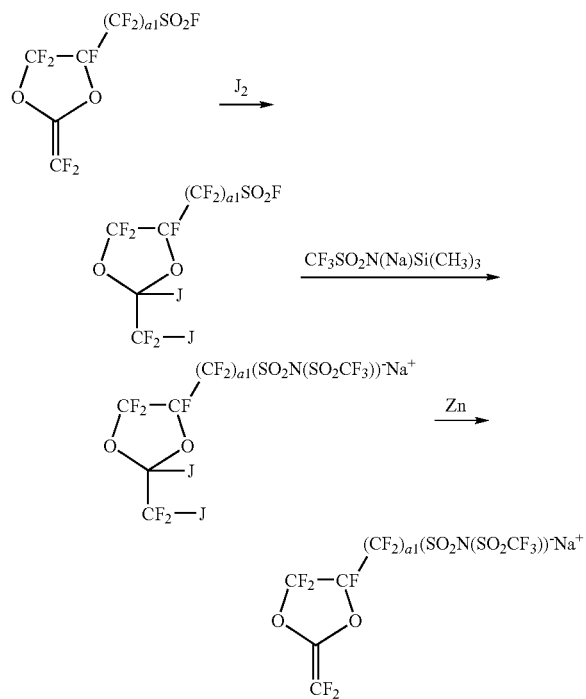

The sulfonimide group in a salt form can be converted to an acid form by treatment with an acid such as sulfuric acid, nitric acid or hydrochloric acid.

Further, it is also possible to obtain a polymer electrolyte material having sulfonimide groups by polymerizing the compound (a) to synthesize a polymer having —SO$_2$F groups and applying the same treatment to the —SO$_2$F groups of the polymer.

Further, the polymer constituting the polymer electrolyte material of the present invention may be subjected to stabilization of unstable sites at e.g. polymer ends by fluorination with fluorine gas or by heat treatment in the presence of air and/or water, after the polymerization, in order to improve the durability, etc. Such a method for converting the groups or polymer treatment may be carried out in accordance with known methods and conditions.

The present electrolyte material is formed into a membrane form and may be used as a polymer electrolyte membrane. The method for forming it into a membrane form is not particularly limited, and the polymer electrolyte material may be dissolved or dispersed in a solvent, and the obtained liquid may be formed into a membrane by casting, or such a membrane may be obtained by an operation such as extrusion, stretching or the like. For the extrusion, it is preferred to employ a polymer having —SO$_2$F groups as a precursor for the polymer electrolyte material from the viewpoint of the excellent melt flowability, and to convert it after molding to the solid polymer electrolyte membrane by hydrolysis.

Further, the polymer electrolyte membrane may be reinforced by a porous body, fiber, woven fabric, non-woven fabric, etc. of e.g. polytetrafluoroethylene (PTFE), tetrafluoroethylene/hexafluoropropylene copolymer (FEP), tetrafluoroethylene/perfluoro(alkoxy vinyl ether) copolymer (PFA), polyethylene, polypropylene or polyphenylene sulfide (PPS). An ionic group-containing polymer membrane thus obtained may be treated with an aqueous hydrogen peroxide solution, as the case requires.

Further, as a method for further improving the durability of the electrolyte membrane, it is also preferred to add at least one type of atoms selected from the group consisting of cerium and manganese to the electrolyte membrane. Cerium or manganese is considered to have an effect to decompose hydrogen peroxide as a substance to cause deterioration of the electrolyte membrane. Cerium or manganese is particularly preferably present in the form of ions in the membrane.

Cerium ions or manganese ions may be present in any state in the electrolyte membrane so long as they are present in the form of ions. And, as one method, part of sulfonic acid groups in a cation exchange membrane may be present as ion-exchanged by cerium ions or manganese ions. The electrolyte membrane is not required to uniformly contain cerium ions or manganese ions. Accordingly, it may be a cation exchange membrane wherein at least two layers made of a polymer compound having sulfonic acid groups, are laminated, and at least one layer among such at least two layers may be made of a cation exchange membrane wherein at least some of sulfonic acid groups are ion-exchanged by cerium ions or manganese ions. For example, particularly in a case where it is desired to increase the durability against hydrogen peroxide or peroxide radicals with respect to the anode side, only the layer closest to the anode may be made to be a layer made of an ion exchange membrane containing cerium ions or manganese ions.

As the electrolyte membrane contains cerium ions or manganese ions, it has excellent resistance against hydrogen peroxide or peroxide radicals. The reason for such excellent resistance is not clearly understood, but it is considered that as the electrolyte membrane contains cerium ions or manganese ions, particularly as some of sulfonic acid groups are ion exchanged by cerium ions or manganese ions, the interaction between cerium ions or manganese ions and $-SO_3^-$ effectively will improve the resistance of the electrolyte membrane against hydrogen peroxide or peroxide radicals. As a result, the electrolyte membrane has excellent resistance against hydrogen peroxide or peroxide radicals, whereby a polymer electrolyte fuel cell provided with a membrane-electrode assembly having such an electrolyte membrane of the present invention, is excellent in durability and capable of stable power generation over a long period of time.

Further, cerium or manganese will improve the durability of the electrolyte membrane even if it is present in the membrane in a state of particles of its oxide or phosphate.

Further, cerium atoms or manganese atoms are effective to improve the durability of a polymer electrolyte fuel cell even if they are contained in the catalyst layers.

Further, to the electrolyte membrane of the present invention, silica, zirconium phosphate or a heteropolyacid such as phosphorus molybdic acid or phosphorus tungstic acid may be incorporated as a humectant to prevent drying.

The present electrolyte material can be well dissolved or dispersed in an organic solvent having a hydroxyl group. The organic solvent having a hydroxyl group is not particularly limited, but an organic solvent having an alcoholic hydroxyl group is preferred.

The organic solvent having an alcoholic hydroxyl group may, for example, be methanol, ethanol, 1-propanol, 2-propanol, 2,2,2-trifluoroethanol, 2,2,3,3,3-pentafluoro-1-propanol, 2,2,3,3-tetrafluoro-1-propanol, 4,4,5,5,5-pentafluoro-1-pentanol, 1,1,1,3,3,3-hexafluoro-2-propanol, 3,3,3-trifluoro-1-propanol, 3,3,4,4,5,5,6,6,6-nonafluoro-1-hexanol or 3,3,4,4,5,5,6,6,7,7,8,8,8-tridecafluoro-1-octanol. Further, as an organic solvent other than an alcohol, an organic solvent having a carboxyl group such as acetic acid may also be used.

Here, as the organic solvent having a hydroxyl group, the above-mentioned solvent may be used alone, or two or more of such solvents may be used as mixed. Further, it may be used in combination with water or another fluorinated solvent. As such another fluorinated solvent, fluorinated solvents exemplified as preferred fluorinated solvents in the above-described solution polymerization reaction in the production of a polymer electrolyte material, may be mentioned. In a case where the organic solvent having a hydroxyl group is to be used as a solvent mixture with water or another fluorinated solvent, the content of the organic solvent having a hydroxyl group is preferably at least 10%, more preferably at least 20%, based on the total mass of the solvents.

Further, in such a case, the present electrolyte material may be dissolved or dispersed in the solvent mixture from the beginning. However, the present electrolyte material may firstly be dissolved or dispersed in an organic solvent having a hydroxyl group, and then water or another fluorinated solvent may be mixed thereto. Further, dissolution or dispersion of the present electrolyte material in such a solvent is preferably carried out within a temperature range of from 0 to 250° C., more preferably from 20 to 150° C., under the atmospheric pressure or under a condition closed and pressurized by e.g. an autoclave. In a case where an organic solvent having a boiling point lower than water is incorporated, water may be added after or during distilling off the solvent to substitute water for the solvent.

A liquid composition obtained by using such a solvent is useful for preparing a cast membrane made of the polymer electrolyte material or for preparing catalyst layers for a polymer electrolyte fuel cell. In the case of preparing catalyst layers, a liquid obtained by mixing a catalyst to the liquid composition may be coated. In such a case, the content of the polymer electrolyte material in the liquid composition is preferably from 1 to 50%, more preferably from 3 to 30%, based on the total mass of the liquid composition. If it is less than 1%, it will be necessary to increase the number of coating operations in order to obtain a desired thickness in the preparation of the membrane or catalyst layers, or the time for removal of the solvent will be prolonged, thus it tends to be difficult to conduct the production operation efficiently. On the other hand, if it exceeds 50%, the viscosity of the liquid composition tends to be too high, and the handling efficiency tends to be poor.

Such a liquid composition may be prepared even when the counter ions of the present electrolyte material are substituted by monovalent metal cations other than $H^+$ or by ammonium ions wherein at least one hydrogen atom may be substituted by a hydrocarbon group. In such a case, after forming the electrolyte membrane or catalyst layers, the counter ions may be converted to H+ by treatment with an acid such as hydrochloric acid, nitric acid or sulfuric acid. The monovalent metal cations may, for example, be $Li^+$, $Na^+$ or $K^+$, and the ammonium ions may, for example, be trimethyl ammonium ions, triethyl ammonium ions, tributyl ammonium ions, or tetramethyl ammonium ions.

Further, to the liquid composition, in addition to the present electrolyte material, a resin which will be a polymer electrolyte material other than the present electrolyte material, may also be incorporated.

The polymer electrolyte material of the present invention may be used not only for hydrogen/oxygen type fuel cells, but also for direct methanol type fuel cells (DMFC). Methanol or a methanol aqueous solution to be used as a fuel for DMFC may be a liquid feed or a gas feed.

Further, the present invention provides a polymer containing the following monomer units (M) (hereinafter referred to as the polymer M) (wherein m1 is an integer of from 1 to 6, and the same applies hereinafter).

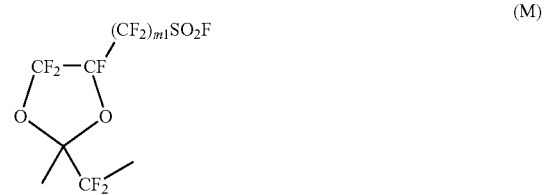

(M)

The following monomer units may be mentioned as specific examples of the monomer units (M):

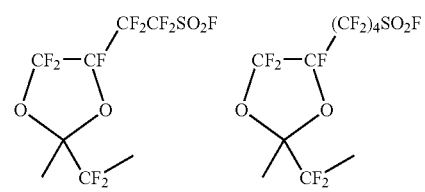

The polymer M can be produced by polymerizing the following compound (m). The polymer obtained by polymerizing the compound (m) is a polymer containing units (M). The method for the polymerization reaction of the compound (m) is preferably carried out in accordance with the method disclosed in WO03/37885. The process for producing the compound (m) will be described hereinafter.

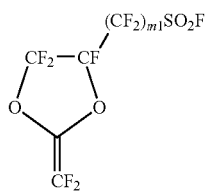

In the compound (m), m1 is an integer of from 1 to 6, preferably an integer of from 1 to 4, particularly preferably an integer of from 2 to 4. The compound (m) of the present invention is characterized in that the number m1 for the group represented by the formula —$(CF_2)_n$— as the group separating the dioxolane skeleton and the —$SO_2F$ group, is small, and groups other than the group represented by the formula —$(CF_2)_nSO_2F$ bonded to the dioxolane skeleton are fluorine atoms. Accordingly, the polymer obtained by polymerizing the compound (m) can realize the characteristics such as a high softening temperature and high mechanical strength.

The following compounds may be mentioned as specific examples of the compound (m):

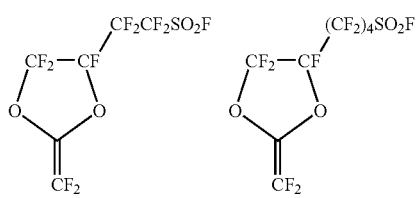

The mass average molecular weight of the polymer M of the present invention is preferably from $5 \times 10^3$ to $5 \times 10^6$, particularly preferably from $1 \times 10^4$ to $3 \times 10^6$.

The polymer M of the present invention may be a polymer comprising at least one type of units (M) or a polymer comprising at least one type of units (M) and at least one type of units other than units (M) (hereinafter referred to as other units M). The latter polymer (M) is preferably a polymer comprising one type of units (M) and at least one type of other units M.

In a case where the polymer M is a copolymer comprising at least two types of units, arrangement of the respective units may be a block-form, a graft form or a random form. Among them, from the viewpoint of the usefulness of the polymer M, arrangement of the respective units is preferably a random-form.

The polymer M which is a polymer having other units M, is preferably prepared by copolymerizing the compound (m) with another monomer copolymerizable with the compound (m) (hereinafter referred to as another monomer m). Other units M may be units containing substantially no hydrogen atoms or units containing hydrogen atoms. From the viewpoint of the durability when the polymer M is used as a material for an ion exchange membrane, other units are preferably units containing substantially no hydrogen atoms. The units containing substantially no hydrogen atoms may more preferably be units obtained by polymerizing $CF_2$=$CF_2$, $CF_2$=$CFOCF_2CF_2CF$=$CF_2$ or perfluoro(2,2-dimethyl-1,3-dioxole). From such a viewpoint that the softening temperature of the polymer becomes high, particularly preferred is one containing units obtained by polymerizing $CF_2$=$CF_2$ or perfluoro(2,2-dimethyl-1,3-dioxole).

The proportion of units (M) to the total units in the polymer (M) may suitably be changed depending upon the particular application of the polymer M. In a usual case, the proportion of units (M) to the total units in the polymer (M) is preferably from 0.1 to 100 mol %, and in a case where other units M are required, it is preferably from 5 to 90 mol %, particularly preferably from 5 to 50 mol %. The proportion of other units M is preferably at most 99.9 mol %, more preferably from 10 to 95 mol %.

In a case where the polymer (M) is to be used as a material for an ion exchange membrane, the proportion of units (M) is preferably adjusted within the following range depending upon the structure or particular application of the polymer (M).

In a case where the polymer (M) is a non-crosslinked polymer, from such a viewpoint that high power generation efficiency can be obtained with a low resistance, the proportion of units (A) to the total units in the polymer (M) is preferably at least 5 mol %, particularly preferably at least 10 mol %. Further, from the viewpoint of the mechanical properties, the proportion of units M to the total units in the polymer (M) is preferably at most 50 mol %, particularly preferably at most 35 mol %.

In a case where the polymer (M) is to be used as a material for an ion exchange membrane, some or all (preferably all) of the —$SO_2F$ groups are converted to —$SO_3H$ groups before use. The conversion of —$SO_2F$ groups can be carried out in accordance with a known method. For example, a method of alkali hydrolysis treatment, followed by acid treatment, may be mentioned. This method is preferably carried out in accordance with the method disclosed in WO03/37885.

The polymer (M) having —$SO_2F$ groups converted to —$SO_3H$ groups, has a structure in which one of the carbon atoms constituting the main chain is a carbon atom forming a perfluoro(1,3-dioxolane) skeleton, and the carbon atom at the 4-position of the skeleton is substituted by a group represented by the formula —$(CF_2)_nSO_3H$ (wherein n is as defined above). Such a polymer (M) is excellent in the mechanical strength and softening temperature and has proton conductivity. Accordingly, the polymer (M) of the present invention is useful as the above-mentioned electrolyte material for polymer electrolyte fuel cells, i.e. as an electrolyte material to be used for membranes or catalyst layers for fuel cells. Such a polymer (M) can also be used for membranes for brine electrolysis.

As a process for producing the compound (m), the following process may be mentioned wherein the following compound (m-3) is converted to the following compound (m-2) by a liquid phase fluorination reaction, and then the compound (m-2) is converted to the following compound (m-1) by an ester decomposition reaction, and then the compound (m-1) is subjected to a thermal decomposition reaction (wherein $R^{EF}$ represents a fluorinated monovalent organic group).

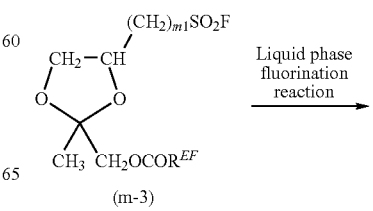

-continued

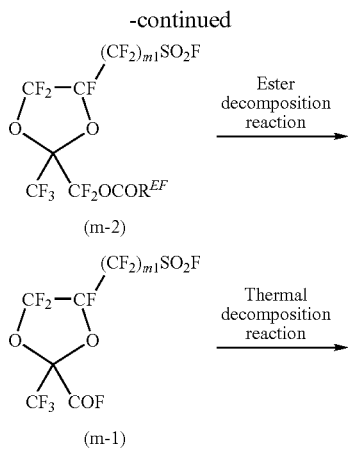

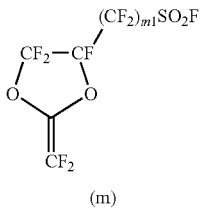

The liquid phase fluorination reaction, ester decomposition reaction and thermal decomposition reaction are preferably carried out in accordance with the methods disclosed in WO03/37885.

$R^{EF}$ may, for example, be —$CF_2CF_3$, —$CF(CF_3)CF_2CF_3$, —$CF(CF_3)_2$, —$CF(CF_3)O(CF_2)_3F$ or —$CF(CF_3)OCF_2CF(CF_3)O(CF_2)_3F$.

The process for producing the compound (m-3) is not particularly limited, and for example, a process via the following reaction route employing the following compound (m-7) as the starting material, may be mentioned.

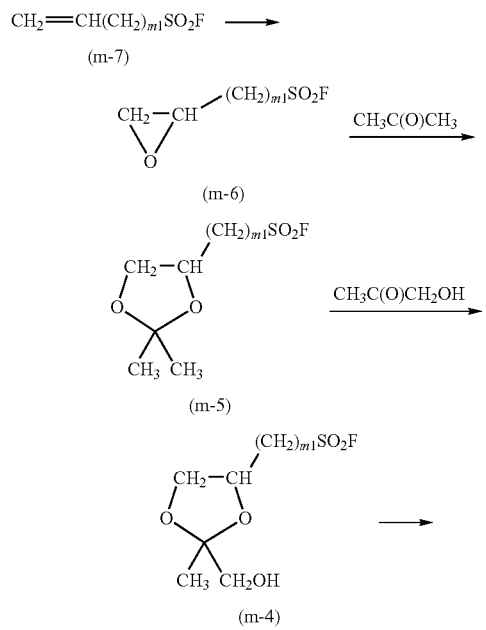

-continued

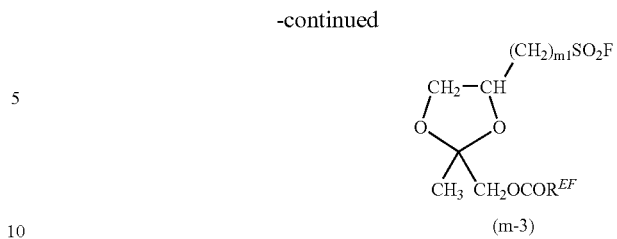

The process for producing the compound (m-7) as the starting material in the above process, is not particularly limited. For example, a process via the following reaction route employing the following compound (m-12) as a starting material, is preferred.

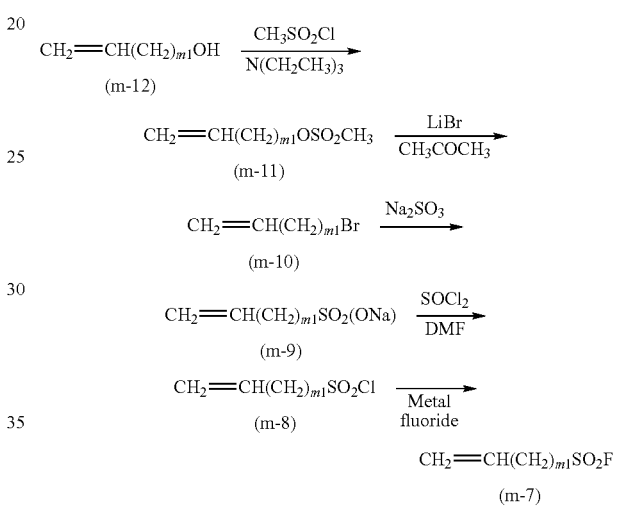

The following compounds may be mentioned as specific examples of the compound (m-12):

$CH_2$=$CHCH_2SO_2F$,

$CH_2$=$CHCH_2CH_2SO_2F$,

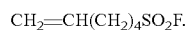
$CH_2$=$CH(CH_2)_4SO_2F$.

Further, the present invention provides a polymer containing the following monomer units (P) (hereinafter referred to as the polymer P) (wherein p1 represents an integer of from 1 to 6, preferably from 2 to 4, and the same applies hereinafter).

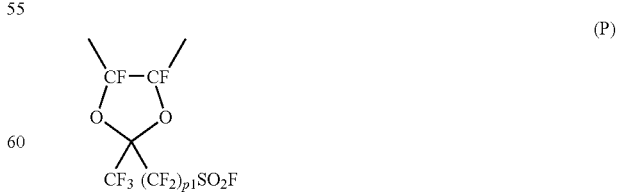

The following monomer units may be mentioned as specific examples of the monomer units (P):

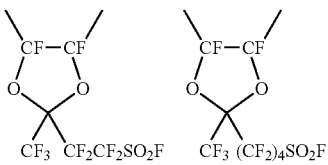

The polymer P is preferably produced by polymerizing the following compound (p). The polymerization of the compound (p) is preferably carried out by a method of polymerizing the compound (p) in the presence of a radical initiator. As the radical initiator, a peroxide, an azo-compound or a persulfate may, for example, be used. The process for producing the compound (p) will be described hereinafter.

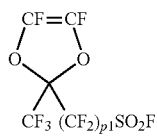
(p)

The following compounds may be mentioned as specific examples of the compound (p):

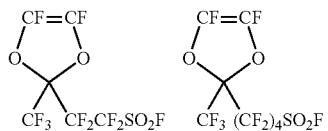

The polymer P may be a polymer comprising monomer units (P), or a copolymer comprising monomer units (P) and monomer units other than the monomer units (P) (hereinafter referred to simply as other monomer units P), and it is preferably the copolymer.

In a case where the polymer P is the copolymer, the proportion of monomer units (P) to the total monomer units in the polymer P is preferably from 5 to 50 mol %, more preferably from 5 to 40 mol %, particularly preferably from 10 to 30 mol %, from the viewpoint of the improvement in the solubility, the dimensional stability, etc. of the after-mentioned fluoropolymer. Further, the proportion of other monomer units to the total monomer units in the polymer P is preferably from 50 to 95 mol %, more preferably from 60 to 95 mol %, particularly preferably from 70 to 90 mol %.

The copolymer is preferably produced by polymerizing the compound (p) with a monomer co-polymerizable with the compound (p), other than the compound (p) (hereinafter referred to simply as another monomer p). Arrangement of the respective monomer units in the copolymer may be a random form or a block form, and preferably a random form from the viewpoint of the convenience of polymerization.

Other monomer units P may or may not contain fluorine atoms. From the viewpoint of the heat resistance, water resistance, solvent resistance and durability of the after-mentioned fluoropolymer, other monomer units P containing fluorine atoms are preferred. From the viewpoint of the molding processability, other monomer units P containing no fluorine atoms are preferred.

Other monomer units P containing fluorine atoms are preferably monomer units formed by polymerization of another monomer p containing fluorine atoms.

Such another monomer p containing fluorine atoms is preferably $CF_2{=}CF_2$, $CH_2{=}CF_2$, a monomer having a perfluoro(2-methylene-1,3-dioxolane) structure or a monomer having a perfluoro(1,3-dioxole) structure.

In a case where the after-mentioned fluoropolymer synthesized from the polymer P which is a copolymer, is to be used for the polymer electrolyte for fuel cells, another monomer p containing fluorine atoms is preferably $CF_2{=}CF_2$ from the viewpoint of the durability, or is preferably a monomer having a perfluoro(2-methylene-1,3-dioxolane) structure, a monomer having a perfluoro(1,3-dioxole) structure or $CF_2{=}CFOCF_2CF_2CF{=}CF_2$ from the viewpoint of the gas permeability and softening temperature.

In a case where the polymer P is a copolymer, another monomer p or a combination of such other monomers p is preferably $CF_2{=}CF_2$ only, or a combination of $CF_2{=}CF_2$ and a monomer having a perfluoro(2-methylene-1,3-dioxolane) structure, a monomer having a perfluoro(1,3-dioxole) structure or $CF_2{=}CFOCF_2CF_2CF{=}CF_2$.

The lower limit of the number average molecular weight of the polymer P is preferably 5,000, more preferably 10,000, particularly preferably 20,000, from the viewpoint of the mechanical strength. The upper limit of the number average molecular weight of the polymer P is preferably 5,000,000, more preferably 2,000,000, from the viewpoint of the solubility in a solvent and the molding processability of the after-mentioned fluoropolymer.

Further, the value of the molecular weight of the polymer P converted to the molecular weight per one $-SO_2F$, is preferably from 500 to 1,500, more preferably from 550 to 1,200, particularly preferably from 600 to 900, from the viewpoint of the water resistance, durability, dimensional stability, etc. of the after-mentioned fluoropolymer.

The polymer P of the present invention is a polymer essentially containing $-SO_2F$ groups, and a fluoropolymer excellent in ion conductivity can be obtained by chemically converting some or all (preferably all) of the $-SO_2F$ groups to $-SO_3H$. Such a polymer can be preferably used as a material for a polymer electrolyte (particularly as the above-described electrolyte material for polymer electrolyte fuel cells).

As a process for producing the compound (p), a process may be mentioned wherein the following compound (p-6) is reacted in the presence of oxygen gas to obtain the following compound (p-5), then the compound (p-5) is reacted in the presence of aluminum chloride or aluminum fluorochloride to obtain the following compound (p-4), then the compound (p-4) is reacted with $CH_2(OH)CH_2Cl$ to obtain the following compound (p-3), then the compound (p-3) is reacted with chlorine gas to obtain the following compound (p-2), then the compound (p-2) is reacted in the presence of antimony trifluoride and antimony pentachloride to obtain the following compound (p-1), and then the compound (p-1) is subjected to a dechlorination reaction in the presence of zinc.

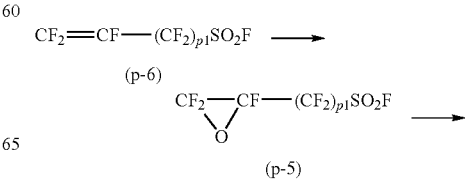

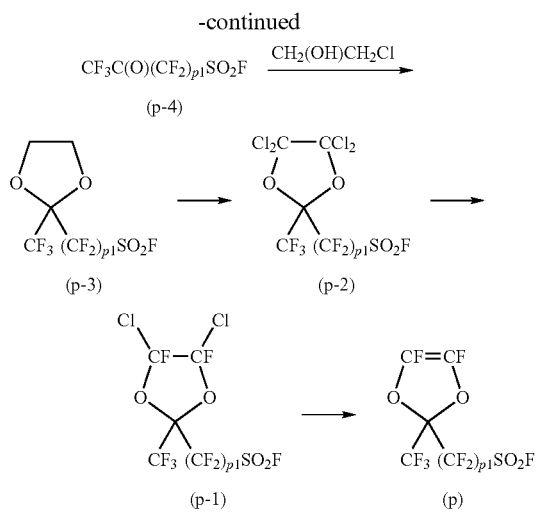

EXAMPLES

Now, the present invention will be described in further detail with reference to Examples, but it should be understood that the present invention is by no means restricted thereto.

Further, in the following, 1,1,2-trichlorotrifluoroethane will be represented by R-113, $CClF_2CF_2CHClF$ by R-225cb, $CF_2=CF_2$ by TFE, $CF_2=CFOCF_2CF(CF_3)OCF_2CF_2SO_2F$ by PSVE, $((CH_3)_2CHOC(O)O)_2$ by IPP, and azobisisobutyronitrile by AIBN. The pressure is represented by a gauge pressure unless otherwise specified.

The purity was obtained from the peak area ratio by a gas chromatography analysis. The reaction yield of a fluoro compound was obtained by a $^{19}F$-NMR analysis using perfluorobenzene as standard.

Production Example of Compound (m4)

The following compound (m4) was produced via the following reaction route.

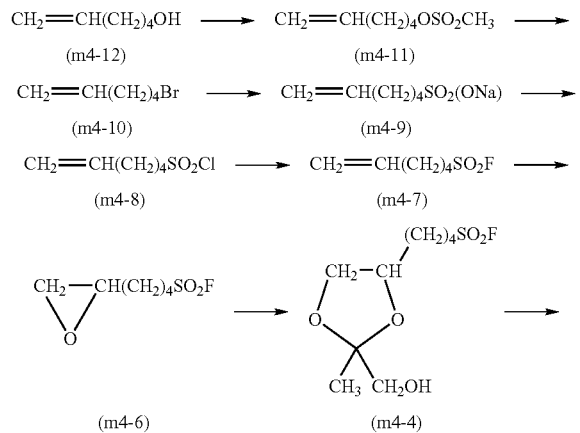

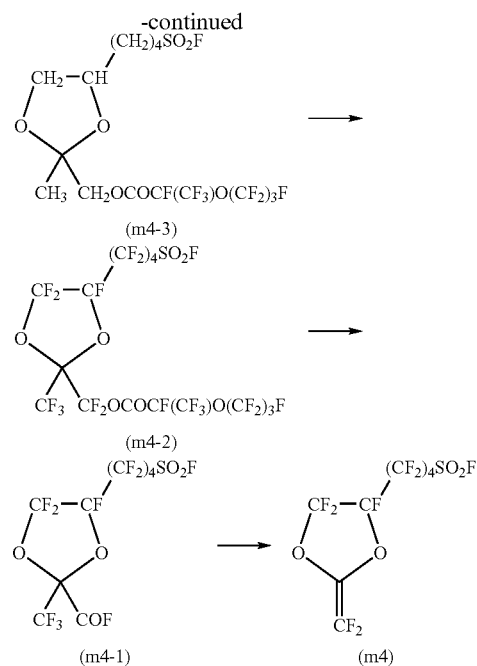

Production of Compound (m4-11)

Into a four-necked round bottom flask (internal capacity: 2 L) equipped with a dropping funnel, a thermometer and a stirring bar, 100 g of the compound (m4-12) having a purity of 91%, 500 g of $CH_2Cl_2$ and 112 g of $N(CH_2CH_3)_3$ were charged in a nitrogen atmosphere. Then, while the internal temperature of the four-necked round bottom flask was maintained at from 10 to 20° C. in an ice bath, 115 g of $CH_3SO_2Cl$ was dropwise added over a period of 30 minutes with stirring. Further, while the internal temperature of the four-necked flask was maintained at 25° C., stirring was continued for two hours.

Then, 500 g of deionized water was added to the four-necked round bottom flask to obtain a double layered liquid. The lower layer of the double layered liquid was recovered and after dehydration with magnesium sulfate, distilled under reduced pressure to obtain a crude product (174 g). The crude product was analyzed by $^1H$-NMR and gas chromatography, whereby formation of the heading compound (purity 91%) was confirmed.

Production of Compound (m4-10)

Into a four-necked round bottom flask (internal capacity: 2 L) equipped with a Dimroth condenser, a dropping funnel, a thermometer and a stirring bar, 173 g of the above-mentioned crude product and 350 g of $CH_3COCH_3$ were charged in a nitrogen gas atmosphere. Then, while the internal temperature of the four-necked round bottom flask was maintained at 20° C., 169 g of LiBr was gradually added with stirring. Further, the solution in the flask was refluxed under heating for one hour.

The solution in the flask was subjected to filtration, and the filtrate was put into a flask. The flask was heated under the atmospheric pressure to distill off the solvent in the solution. When the flask was cooled, crystals precipitated. Therefore, the solution in the flask was subjected to filtration to have crystals and a filtrate separated. Water was added to crystals to obtain a double layered liquid. The filtrate and the upper layer liquid of the double layered liquid were mixed and after dehydration with magnesium sulfate, distilled under reduced pressure to obtain 101 g of a fraction of from 71 to 73° C./6.7 kPa (absolute pressure). The fraction was analyzed by $^1$H-NMR and gas chromatography, whereby formation of the heading compound (purity: 91.5%) was confirmed.

Production of Compound (m4-9)

Into a four-necked round bottom flask (internal capacity: 1 L) equipped with a Dimroth condenser, a thermometer and a stirring bar, 283 g of deionized water and 68.6 g of $Na_2SO_3$ were charged and stirred for dissolution. Then, 88.5 g of the above-mentioned distillation fraction was added, and the solution in the flask was refluxed under heating for 6 hours. After the majority of water was distilled off under reduced pressure by an evaporator, toluene was added, and distillation under reduced pressure was continued. Further, vacuum drying (100° C.) was carried out for 12 hours to obtain 151 g of a white solid containing the heading compound and NaBr as the main components. The white solid was analyzed by $^1$H-NMR, whereby formation of the heading compound was confirmed.

Production of Compound (m4-8)

Into a four-necked round bottom flask (internal capacity: 1 L) equipped with a Dimroth condenser, a thermometer and a stirring bar, 356 g of $CH_2Cl_2$, 70 g of the above white solid and 0.70 g of dimethylformamide were charged in a nitrogen atmosphere. While the internal temperature of the four-necked round bottom flask was maintained at from 19 to 22° C., 144 g of $SOCl_2$ was dropwise added over a period of 10 minutes with stirring. Further, the solution in the flask was refluxed under heating for 7.5 hours.

Then, ice water (about 1.5 L) was added to the four-necked round bottom flask to obtain a double layered liquid. The lower layer liquid of the double layered liquid, and an extracted liquid having the upper layer liquid extracted with $CH_2Cl_2$ (350 g), were mixed and after dehydration with magnesium sulfate, concentrated to obtain a concentrated product. Further, the concentrated product was subjected to distillation at 25° C. to distill off the solvent by a vacuum pump to obtain a liquid (43 g). The liquid was analyzed by $^1$H-NMR, whereby formation of the heading compound was confirmed.

Production of Compound (m4-7)

Into a four-necked round bottom flask (internal capacity: 300 mL) equipped with a Dimroth condenser, a thermometer and a stirring bar, 42 g of the above liquid and 100 g of $CH_3CN$ were charged in a nitrogen gas atmosphere. While 27 g of KF (manufactured by Morita Chemical Industries Co., Ltd., tradename: Chlorocatch F) was added to the four-necked round bottom flask, with stirring, and further refluxing under heating was carried out for 8 hours.

The solution in the flask was subjected to filtration, and the filtrate was concentrated. 100 g of deionized water was added to the concentrated product, followed by stirring to obtain a double layered liquid. The lower layer liquid of the double layered liquid was recovered and after dehydration with magnesium sulfate, distilled to obtain 24 g of a fraction of 75° C./0.86 kPa (absolute pressure). The fraction was analyzed by $^1$H-NMR, $^{19}$F-NMR and gas chromatography, whereby formation of the heading compound (purity: 96.5%) was confirmed.

Production of Compound (m4-6)

Into a 300 mL four-necked round bottom flask equipped with a Dimroth condenser, a thermometer and a stirring bar, 12.7 g (77 mmol) of the compound (m4-7) and 150 mL of dichloromethane were added in a nitrogen atmosphere, and 22 g (80 mmol) of metachloroperbenzoic acid was added with stirring in a water bath. After stirring overnight, the crude liquid was subjected to filtration, and the filtrate was washed twice with 100 mL of a saturated sodium hydrogen carbonate aqueous solution and further once with a 100 mL of a saturated sodium chloride aqueous solution. The crude liquid after washing was dried over sodium sulfate and then subjected to filtration, whereupon the solvent was removed by an evaporator, and distillation was carried out to obtain 12.88 g (71 mmol, GC purity: 95%) of the heading compound. Boiling point: 89° C./0.70 kPa (absolute pressure).

Production of Compound (m4-4)

Into a 100 mL three-necked flask equipped with a Dimroth condenser, a thermometer and a stirring bar, 14 g (78 mmol) of the compound (m4-6) and 15 mL of acetone were charged in a nitrogen atmosphere, and 40 mg (28 mmol) of boron trifluoride etherate was added with stirring in a water bath. After 6 hours, it was confirmed that a reaction conversion reached 97%.

Then, 10 g (140 mmol) of hydroxyacetone was gradually added, and while withdrawal of low boiling point components was carried out at 67° C. under 13 kPa (absolute pressure), stirring was carried out for 10 hours. The crude liquid was cooled and then, after adding 100 mL of a saturated sodium hydrogen carbonate aqueous solution, extracted twice with 100 mL of t-butylmethyl ether and further washed with 100 mL of a saturated sodium chloride aqueous solution. The product was dried over sodium sulfate and then subjected to filtration. The solvent was distilled off by an evaporator, and further, vacuum drying was carried out to obtain 15 g of the compound (m4-4).

Production of Compound (m4-3)

Into a 100 mL three-necked flask equipped with a dropping funnel, a condenser, a thermometer and a stirring bar, 3.3 g (79 mmol) of sodium fluoride and 10 g (39 mmol) of the compound (m4-4) were added in a nitrogen atmosphere and stirred for 5 minutes in an ice bath. Then, 13 g (39 mmol) of $F(CF_2)_3OCF(CF_3)COF$ was dropwise added. The reaction crude liquid was diluted with dichloropentafluoropropane, followed by filtration and concentration to obtain 21 g of the compound (m4-3).

Production of Compound (m4-2)

Into an autoclave (internal capacity: 3,000 mL, made of nickel), 1,700 g of R-113 was put and stirred, and the temperature in the autoclave was maintained at 25° C. At the gas outlet of the autoclave, a condenser maintained at 20° C., a NaF pellet-packed layer and a condenser maintained at −10° C. were installed in series. Further, a liquid-returning line was installed to return the condensed liquid from the condenser maintained at −10° C. to the autoclave. After supplying nitrogen gas into the autoclave at 25° C. for one hour, fluorine gas diluted to 20% with nitrogen gas (hereinafter referred to as 20% fluorine gas) was further supplied at 25° C. for one hour at a flow rate of 16.24 L/hr.

Then, while 20% fluorine gas was supplied at the same flow rate to the autoclave, a solution having 45 g of the compound (m4-3) dissolved in 650 g of R-113, was injected over a period of 24.1 hours. Further, while 20% fluorine gas was supplied at the same flow rate, the pressure in the autoclave was raised to 0.15 MPa, and 30 mL of a R-113 solution having a benzene concentration of 0.01 g/mL was injected under heating from 25° C. to 40° C. Then, while the pressure in the autoclave was maintained at 0.15 MPa and the temperature in the autoclave was maintained at 40° C., 20 mL of R-113 was supplied so that the benzene solution in the piping was all injected into the autoclave. The total amount of benzene injected was 0.3 g, and the total amount of R-113 injected was 50 mL.

Further, stirring was continued for one hour while 20% fluorine gas was supplied into the autoclave at the same flow rate. Then, the pressure in the autoclave was adjusted to 0 MPa (gauge pressure), and nitrogen gas was supplied for one hour. The content in the autoclave was analyzed by $^{19}$F-NMR, whereby formation of the compound (m4-2) was confirmed. The yield was 60%.

Production of Compound (m4-1)

The reaction solution containing 72.5 g of the compound (m4-2) was charged into a flask together with 2.05 g of a KF powder and heated at 80° C. for 1.5 hours and at from 90 to 95° C. for 1.5 hours by immersing in an oil bath with vigorous stirring. After cooling the flask, distillation under reduced pressure was carried out to obtain 36.7 g of a fraction of from 80 to 84° C./4.0 kPa (absolute pressure) (hereinafter referred to as fraction X). The yield of the compound (m4-1) was 78.5%, and the purity was 95%.

Production of Compound (m4)

A glass beads-packed fluidized layer type stainless steel reaction tube heated to 320° C. (inner diameter: 1.6 cm, packed height of glass beads: 40.5 cm) was prepared. Then, a gas mixture having the above fraction X, perfluorohexane (manufactured by 3M, tradename, FC-72) and nitrogen gas mixed in a ratio (molar ratio) of fraction X:perfluorohexane:nitrogen gas=2:3:95, was heated to 320° C. and supplied to the reaction tube at a linear velocity of 2.7 cm/s. At the outlet of the reaction tube, a trap equipped with a condenser was installed.

When the gas mixture in an amount corresponding to 11.0 g as the fraction X was supplied, a liquid (19.4 g) was obtained in the trap. The liquid was analyzed by $^{19}$F-NMR, whereby the liquid was confirmed to contain the compound (m4) and perfluorohexane as the main components. The reaction yield of the compound (m4) was 52%.

Further, methanol and water were sequentially added to a mixed liquid (58.2 g) obtained by mixing this liquid and a liquid obtained in a trap by supplying the gas mixture in an amount corresponding to 22.3 g as the fraction X to the reaction tube in the same manner, to obtain a double layered liquid. The organic layer of the double layered liquid was recovered and after drying by a molecular sieve 4A, distilled to obtain a fraction of from 52 to 55° C./1.3 kPa (absolute pressure). The fraction was analyzed by $^{19}$F-NMR, whereby formation of the compound (m4) of high purity was confirmed.

$^{19}$F-NMR of compound (m4) (282.7 MHz, solvent: CDCl$_3$, standard: CFCl$_3$) δ (ppm) 46.3(1F), −81.1(1F), −88.1(1F), −107.5(1F), −108.6(1F), −119.2 to −123.7(6F), −124.8(1F), −125.3(1F), −126.1(1F).

Production Example of Compound (p2)

The following compound (p2) was produced via the following reaction route.

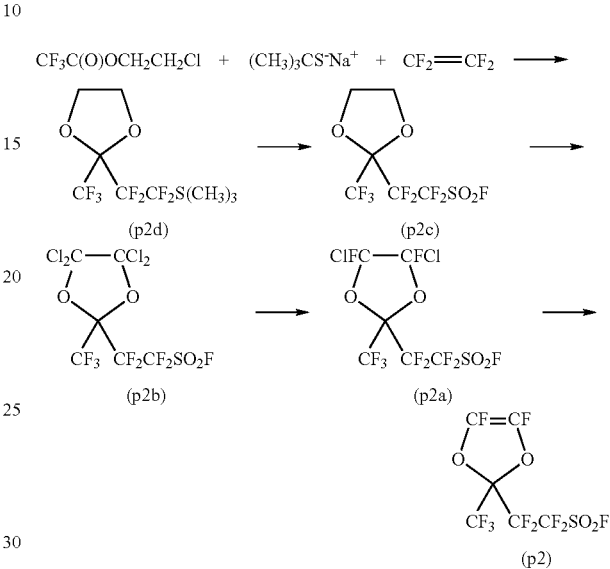

Production of Compound (p2d)

100 g of (CH$_3$)$_3$CS$^-$Na$^+$, 166 g of CF$_3$C(O)OCH$_2$CH$_2$Cl and 1,500 mL of 1,4-dioxane were charged into an autoclave (internal capacity: 2,500 mL) and freeze-deaerated. While the internal temperature of the autoclave was maintained from 20 to 30° C., 200 g of TFE was supplied to the autoclave. A reaction was carried out by stirring the interior of the autoclave at 20° C. for 3 hours and further at 50° C. for two hours. Then, the autoclave was cooled, and TFE was released to terminate the reaction.

The content of the autoclave was put into water, and from the obtained double layered liquid, the lower layer liquid was recovered. The same reaction and recovery were carried out twice, and the obtained lower layer liquid was washed with water, dried over magnesium sulfate and then distilled under reduced pressure to obtain a fraction (253 g) of (80 to 85)° C./(267 to 400) Pa (absolute pressure). The fraction was analyzed, whereby formation of the above compound (p2d) was confirmed.

Production of Compound (p2c)

Into a 75 vol % acetonitrile aqueous solution (1 L) maintained at a temperature of at most 30° C., 200 mL of acetonitrile containing 105 g of the compound (p2d) was dropwise added, while chlorine gas was introduced. After completion of the dropwise addition, introduction of chlorine gas was stopped, and chlorine in the acetonitrile aqueous solution was purged. Then, the acetonitrile aqueous solution was added to excess water to obtain a double layered liquid, whereupon 211 g of the lower layer liquid was recovered.

Then, to 100 g of the lower layer liquid, 200 g of acetonitrile and 150 g of water were added and then 40 g of KHF$_2$ was added, followed by stirring at 25° C. for 48 hours. Then, water was added to obtain a double layered liquid, from which the lower layer liquid was recovered. Further, the lower layer liquid was washed with water, dried over magnesium sulfate and then distilled under reduced pressure to obtain 41 g of a fraction of (53 to 54)° C./(533 to 667) Pa (absolute pressure). The fraction was analyzed, whereby formation of the above compound (p2c) was confirmed.

Production of Compound (p2a)

To 106 g of the fraction obtained in the same manner as the production of the compound (p2c), chlorine gas was bubbled at from 40 to 50° C. under irradiation with a mercury UV lamp, and then, excess chlorine gas was purged to obtain a crude product. The crude product was distilled under reduced pressure to obtain 133 g of a fraction of (74 to 76)° C./(267 to 400) Pa (absolute pressure). The fraction was analyzed by gas chromatography and $^1$H-NMR, whereby formation of the above compound (p2b) was confirmed.

Into a reactor equipped with a reflux condenser, 132 g of the fraction, 17 g of antimony pentachloride and 51 g of antimony trifluoride were added and refluxed under heating at 150° C. for 4 hours. Then, the content of the reactor was subjected to distillation under reduced pressure, and the crude product thereby obtained was washed twice with water and further once with a saturated sodium hydrogen carbonate aqueous solution and then dried over magnesium sulfate. The crude product was distilled under reduced pressure to obtain 110 g of a fraction of 62° C./2133 Pa (absolute pressure). The fraction was analyzed, whereby formation of the above compound (p2a) was confirmed.

Production of Compound (p2)

28 g of dry zinc activated by means of an aqueous hydrochloric acid solution and 90 mL of N,N-dimethylformamide were added to a reactor, and while the internal temperature of the reactor was maintained at 50° C., 4 g of dibromoethane was gradually dropwise added to the reactor. After completion of the dropwise addition, while the internal temperature of the reactor was maintained at 60° C., the internal pressure of the reactor was reduced to 3.6 kPa, and 30 g of the above fraction was dropwise added to the reactor.

The distillate was collected until the distillation of the liquid distilling from the reactor terminated. Further, the internal pressure was reduced to 2 kPa, and the liquid distilled was collected together with said distillate to obtain a reaction crude liquid. The reaction crude liquid was washed with water and dried over magnesium sulfate to obtain a reaction liquid. A similar reaction was repeatedly carried out to obtain 315 g of the reaction liquid in total.

80 g of the reaction liquid was distilled under reduced pressure by means of a spinning band type distiller to obtain 15 g of a fraction of (38 to 39)° C./4 kPa (absolute pressure). The fraction was analyzed, whereby formation of the compound (p2) was confirmed.

$^{19}$F-NMR of compound (p2) (282.7 MHz, solvent: CDCl$_3$, standard: CFCl$_3$) δ (ppm): 46.07(1F), −82.08(3F), −108.12 (2F), −120.89(2F), −158.02(2F).

Synthesis 1 of Polymer

Example 1

Into a stainless steel autoclave having a capacity of 30 cm$^3$, 1.49 g of the compound (m4), 26.8 g of R-225cb containing 67 mg of methanol, and 1.6 mg of IPP were put, cooled with liquid nitrogen and deaerated. After introducing TFE, a reaction was carried out at 40° C. for 6 hours. During this period, the gauge pressure was decreased from 0.6 MPa to 0.5 MPa. After cooling, the gas in the system was purged, and a polymer was precipitated by putting it into hexane. It was washed with hexane and then vacuum-dried at 100° C. to obtain 1.7 g of a white colored polymer.

$A_R$ of the polymer obtained by titration was 1.16 meq/g, and the molar ratio of the following units (M4) to —CF$_2$CF$_2$— units was 19.8:80.2.

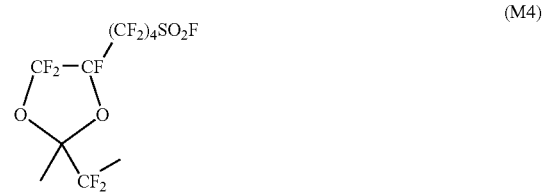

(M4)

Then, the melt fluidity of this polymer was evaluated. Using a flow tester CFT-500A (manufactured by Shimadzu Corporation), a melt extrusion test of the resin was carried out by using a nozzle having a length of 1 mm and an inner diameter of 1 mm under an extrusion pressure of 30 kg/cm$^2$ by changing the temperature, to measure the temperature (hereinafter referred to as TQ) at which the volume flow rate became 100 mm$^3$/sec, which was found to be 333° C.

Fluorine gas (20 vol %) diluted with nitrogen gas was introduced to a gauge pressure of 0.3 MPa and maintained at 180° C. for 4 hours. This polymer was pressed at 300° C. to prepare a film having a thickness of about 100 μm. This film was immersed in a liquid comprising 30% of dimethyl sulfoxide (DMSO), 11% of KOH and 59% of water at 90° C. for 16 hours to convert fluorosulfonyl groups to —SO$_3$K groups. After washing with water, it was immersed in 1 mol/L sulfuric acid and then washed with water to convert —SO$_3$K groups to sulfonic acid groups and further dried to obtain a membrane having sulfonic acid groups.

With respect to this membrane, the softening temperature was measured. Using a dynamic viscoelasticity analyzer DVA200, manufactured by ITK Co., Ltd., the measurement of the dynamic viscoelasticity was carried out with a specimen width of 0.5 cm and a length of specimen between grips being 2 cm at a measuring frequency of 1 Hz and a temperature raising rate of 2° C./min. The softening temperature T$_1$, obtained from the maximum value of the loss modulus was 124° C. Further, T$_2$ was 224° C., and ΔT was 100° C.

Comparative Example 1

Using a polymer which was a copolymer of TFE and PSVE (a molar ratio of 82.2:17.8 in this order) and which had A$_R$ of 1.1 meq/g when hydrolyzed and converted to an acid form and T$_Q$ of 220° C., it was treated with fluorine gas and subjected to heat pressing to prepare a film, followed by hydrolysis and treatment for conversion to an acid form, to obtain a membrane having sulfonic acid groups, in the same manner as in Example 1. The softening temperature T$_1$ obtained by carrying out the measurement of the dynamic viscoelasticity in the same manner as in Example 1, was 73° C., $T_2$ was 176° C., and $\Delta T$ was 103° C.

Comparative Example 2

Using a polymer which was a copolymer of TFE and $CF_2$=$CFOCF_2CF_2SO_2F$ (a molar ratio of 83.9:16.1 in this order) and which had $A_R$ of 1.25 meq/g when hydrolyzed and converted to an acid form and $T_Q$ of 295° C., it was treated with fluorine gas and subjected to hot pressing to form a film, followed by hydrolysis and treatment for conversion to an acid form to obtain an acid form membrane, in the same manner as in Example 1. The softening temperature $T_1$ obtained by carrying out the measurement of the dynamic viscoelasticity in the same manner as in Example 1, was 110° C., the temperature $T_2$ when the storage modulus decreased to $1\times10^6$ Pa, was 207° C., and $\Delta T$ was 97° C.

Comparative Example 3

Into a stainless steel autoclave having a capacity of 0.1 L, 8.48 g of the following compound (z4), 76.3 g of R-225cb containing 17 mg of methanol, and 170 mg of perfluorobenzoyl peroxide were put, cooled with liquid nitrogen and deaerated. After introducing TFE, the mixture was reacted at 70° C. for 50 minutes. During this period, the gauge pressure decreased from 0.97 MPa to 0.43 MPa. After cooling, the gas in the system was purged, and a polymer was precipitated by putting it in hexane. It was washed with hexane and then vacuum-dried at 100° C. to obtain 14.1 g of a white colored polymer. $A_R$ of the polymer obtained from the sulfur content obtained by an elemental analysis, was 1.12 meq/g.

The volume flow rate of this polymer at 300° C. was measured by means of a flow tester CFT-500A (manufactured by Shimadzu Corporation), and found to be 34 mm³/sec, and $T_Q$ was higher than 300° C.

In the same manner as in Example 1, it was treated with fluorine gas and subjected to hot pressing to prepare a film, followed by hydrolysis and treatment for conversion to an acid form to obtain an acid form membrane. Further, the softening temperature $T_1$, obtained by carrying out the measurement of the dynamic viscoelasticity in the same manner as in Example 1, was 98° C., $T_2$ was 247° C., and $\Delta T$ was 149° C.

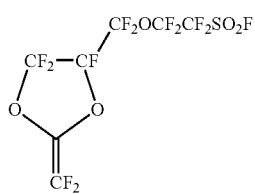

(z4)

Example 2

Into a stainless steel autoclave having a capacity of 100 cm³, 5.73 g of the compound (m4), 108 g of R-225cb containing 11.4 mg of methanol, and 6.4 mg of IPP were put, cooled with liquid nitrogen and deaerated. After introducing TFE, a reaction was carried out at 40° C. for 2 hours and 45 minutes. During this period, the gauge pressure decreased from 0.5 MPa to 0.4 MPa. After cooling, the gas in the system was purged, and a polymer was precipitated by putting it in hexane. After washing with hexane, it was vacuum-dried at 100° C. to obtain 4.9 g of a white colored polymer.

$A_R$ of the polymer was 1.26 meq/g, and the molar ratio of units (M4) to —$CF_2CF_2$— units in the polymer, was 23.0:77.0.

Example 3

In the same manner as in Example 2, a copolymer of the compound (m4) with TFE was synthesized. 2.98 g of the compound (m4), 96.2 mg of methanol, 88.9 g of R-225cb and 5.2 mg of IPP were charged into an autoclave, and TFE was introduced, followed by a reaction for 9 hours. During this period, the pressure decreased from 0.30 MPa to 0.24 MPa. 2.4 g of a white colored polymer was obtained.

$A_R$ of the polymer was 1.42 meq/g, and the molar ratio of units (M4) to —$CF_2CF_2$— units in the polymer, was 28.9:71.1.

Example 4

In the same manner as in Example 2, a copolymer of the compound (m4) with TFE was synthesized. 4.82 g of the compound (m4), 108 g of R-225cb and 5.9 mg of IPP were charged into an autoclave, and TFE was introduced, followed by a reaction for 3.5 hours. During this period, the pressure decreased from 0.29 MPa to 0.22 MPa. 3.0 g of a white colored polymer was obtained.

The molar ratio of the compound (m4) to TFE was 34.8:65.2.

Evaluation 1 of Physical Properties of Polymers

With respect to the polymers of Examples 2 to 4 and Comparative Example 1, membranes having sulfonic acid groups were obtained by carrying out the same treatment as in Example 1. With respect to these membranes, $A_R$, the softening temperatures $T_1$, $T_2$, $\Delta T$ and the results of measurements of the specific resistivity measured by the following method, are summarized in Table 1. The specific resistivity was measured by a known four terminal method with an alternate current of 10 KHz at a voltage of 1 V under a constant temperature and constant humidity condition of 80° C. under a relative humidity of 95% by closely contacting a substrate having four terminal electrodes disposed with a distance of 5 mm to a film having a width of 5 mm.

TABLE 1

| | $A_R$ (meq/g) | $T_1$ (° C.) | $T_2$ (° C.) | $\Delta T$ (° C.) | Specific resistivity (Ωcm) |
|---|---|---|---|---|---|
| Ex. 1 | 1.16 | 124 | 224 | 100 | 5.1 |
| Ex. 2 | 1.26 | 128 | 260 | 132 | 3.7 |
| Ex. 3 | 1.42 | 128 | 184 | 56 | 3.3 |
| Ex. 4 | 1.55 | 132 | 206 | 74 | 2.5 |
| Comp. Ex. 1 | 1.10 | 73 | 176 | 103 | 3.6 |

Process 1 for Preparation of Membrane-Catalyst Layer Assembly

The polymer having —$SO_2F$ groups obtained in Comparative Example 1 was hydrolyzed and converted to an acid form to obtain a polymer having sulfonic acid groups. This polymer was dispersed in ethanol by means of a pressure resistant autoclave having an internal surface made of a hastelloy C alloy, to obtain an ethanol dispersion having a solid content concentration of 10% by mass ratio. This dispersion will be referred to as the electrolyte liquid A. 126 g of water was added to 20 g of a catalyst having platinum supported on a carbon black powder in a mass ratio of 50%, followed by application of ultrasonic waves for 10 minutes to have the catalyst uniformly dispersed. 80 g of the electrolyte liquid A was added thereto, and 54 g of ethanol was further added to bring the solid content concentration to be 10%. This dispersion will be referred to as the coating fluid B for preparation of a cathode catalyst layer. This coating fluid B was applied onto an ETFE substrate film and dried to prepare a cathode catalyst layer having a platinum amount of 0.5 mg/cm$^2$.

Further, 124 g of water was added to 20 g of a catalyst having an alloy of platinum and ruthenium supported in a mass ratio of 53% on a carbon black powder (platinum/ruthenium ratio=30/23), followed by application of ultrasonic waves for 10 minutes to have the catalyst uniformly dispersed, and 75 g of the above electrolyte liquid A was added thereto, and 56 g of ethanol was further added thereto to bring the solid content concentration to be 10% (mass ratio). This dispersion is will be referred to as the coating fluid C for preparation of an anode catalyst layer. This coating fluid C was applied on an ETFE substrate film and dried to prepare an anode catalyst layer having a platinum amount of 0.35 mg/cm$^2$.

The polymer obtained in Example 3 was hot-pressed to prepare a film having a thickness of 50 μm, and in the same manner as in Example 1, the hydrolysis and treatment for conversion to an acid form were carried out to obtain a membrane having sulfonic acid groups. This membrane was sandwiched between the cathode catalyst layer and the anode catalyst layer, followed by hot pressing (pressing conditions: 120° C., two minutes, 3 MPa) to have the two catalyst layers bonded to the membrane, and the substrate films were peeled off to obtain a membrane-catalyst layer assembly having an electrode area of 25 cm$^2$.

Evaluation 1 of Cell Characteristics of Membrane-Electrode Assembly

Figure 3:
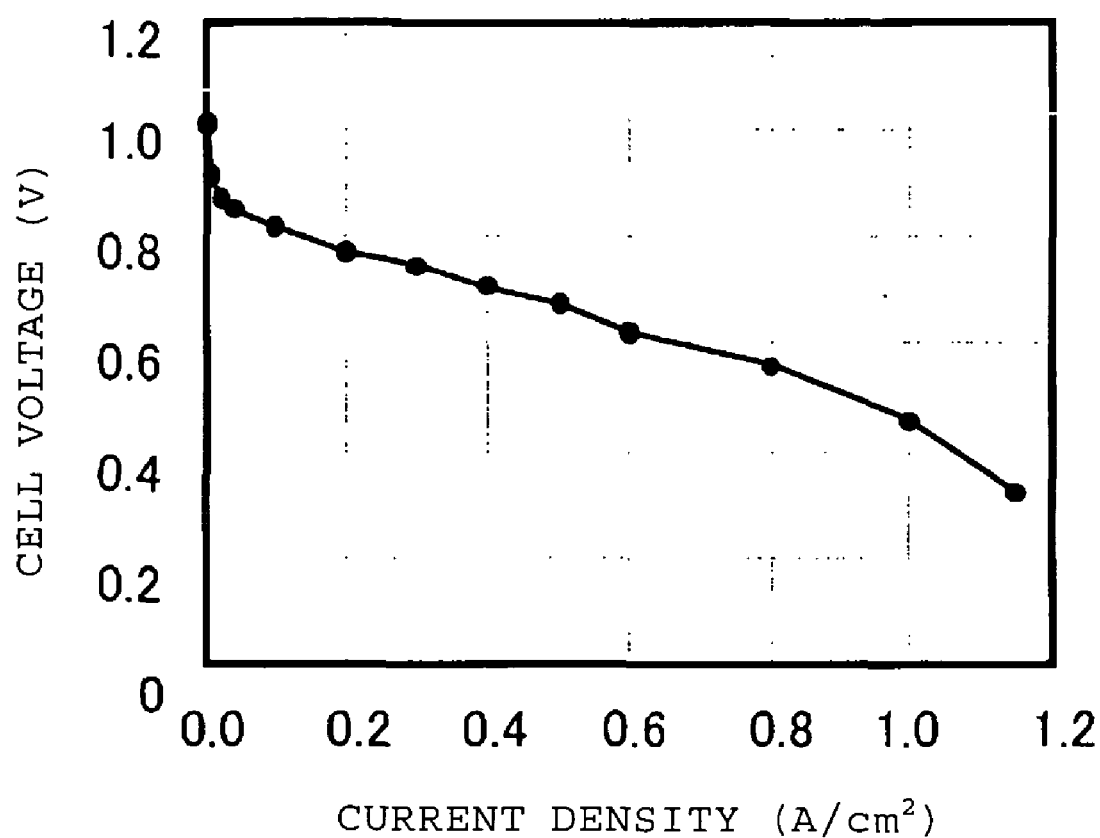
FIG. 3 is a graph showing the current-voltage characteristics at 120° C. of a membrane-electrode assembly having the membrane employing the polymer obtained in Example 3, assembled.

The above membrane-catalyst layer assembly was sandwiched between two gas diffusion layers made of carbon paper to obtain a membrane-electrode assembly. The carbon paper used here had a layer comprising carbon and PTFE on the surface on one side, and it was disposed so that such a layer was in contact with the catalyst layer of the membrane-catalyst layer assembly. This membrane-electrode assembly was assembled into a cell for power generation, and hydrogen (utilization rate: 50%) and air (utilization rate: 50%) were supplied as humidified gases with a pressure of 0.2 MPa and a dew point of 100° C. into the cell. The cell temperature was set to be 120° C., and the current density was changed, whereby the voltage was recorded. The results are shown in FIG. 3.

Synthesis 2 of Polymers and Evaluation 2 of Physical Properties

Example 5

Into an autoclave (internal capacity: 30 mL), 3.6 g of the compound (p2), 27 g of R-225cb and 15 mg of IPP were charged and freeze-deaerated. Then, the internal temperature of the autoclave was maintained at 40° C., and TFE was introduced until the internal pressure became 0.15 MPa, while the interior of the autoclave was stirred. Then, while TFE was continuously introduced to maintain the internal pressure at 0.15 MPa, the reaction was carried out for 7 hours.

Then, the autoclave was cooled, and the internal pressure was released, whereupon hexane was immediately introduced into the autoclave. The flocculated content in the autoclave was recovered and washed three times with hexane and then vacuum-dried at 80° C. for 12 hours to obtain 3.4 g of a polymer. This polymer was analyzed by 19F-NMR (standard: hexafluorobenzene) and IR, whereby the proportion of the following units (p2) to the total units was 26.4 mol %, and the proportion of —CF$_2$CF$_2$— units was 73.6 mol %.

This polymer was processed into a film having a thickness of 100 μm by a hot pressing method, and the film was immersed in an aqueous solution of a mixture comprising KOH/H$_2$O/DMSO=30/65/5 (mass ratio) at 90° C. for 17 hours. Then, it was washed three times with water at 25° C. and immersed in a 2 mol/L sulfuric acid aqueous solution for two hours. Washing with water and dipping in sulfuric acid were repeated three times, respectively, and further washing with water was carried out three times. Then, the film was dried in air at 80° C. for 16 hours and further vacuum-dried to obtain a slightly brown dried film. The softening temperature of the film was 152° C. by the measurement of the dynamic viscoelasticity.

The resistivity of the above film (5 mm in width) was measured by using a four terminal method wherein the above film (5 mm in width) was closely adhered to a substrate having electrodes disposed in a distance of 5 mm, under alternate current conditions (10 KHz, 1 V) under constant temperature and humidity (80° C., 95% RH), and as a result, it was found to be 3.3 Ω·cm.

Example 6

Into an autoclave (internal capacity: 30 mL), 3.6 g of the compound (p2), 27 g of R-225cb and 15 mg of IPP were charged and freeze-deaerated. Then, the internal temperature of the autoclave was maintained at 40° C., and TFE was introduced until the internal pressure became 0.16 MPa with stirring the interior of the autoclave. Then, TFE was continuously introduced to maintain the inner pressure to be 0.16 MPa, and the reaction was carried out for 4 hours.

Then, the autoclave was cooled, and the internal pressure was released, whereupon hexane was immediately introduced into the autoclave. The flocculated content in the autoclave was recovered, washed three times with hexane, and then vacuum-dried at 80° C. for 12 hours, to obtain 1.8 g of a polymer. This polymer was analyzed by $^{19}$F-NMR (standard: hexafluorobenzene) and IR, whereby the proportion of units (P2) to the total units, was 22.2 mol %, and the proportion of —CF$_2$CF$_2$— units was 77.8 mol %.

The softening temperature of a dried film obtained by the measurement of the dynamic viscoelasticity of the film obtained by the same method as in Example 6 except that this polymer was employed, was 148° C., and the specific resistivity of this film was 3.4 Ω·cm.

Example 7

Into an autoclave (internal capacity: 30 mL), 6.3 g of the compound (p2), 8.9 g of R-225cb and 1.5 mg of AIBN were charged and freeze-deaerated. Then, the internal temperature of the autoclave was maintained at 70° C., and TFE was introduced until the internal pressure became 0.5 MPa while the interior of the autoclave was stirred. Then, TFE was continuously introduced to maintain the internal pressure to be 0.5 MPa, the reaction was carried out for 9.5 hours.

Then, the autoclave was cooled, and the internal pressure was released, whereupon hexane was immediately introduced into the autoclave. The flocculated content in the autoclave was recovered, washed three times with hexane, and then vacuum-dried at 80° C. for 12 hours, to obtain 3.1 g of a polymer. This polymer was analyzed by $^{19}$F-NMR (standard: hexafluorobenzene) and IR, whereby the proportion of monomer units (P2) to the total monomer units, was 33.8 mol %, and the proportion of —$CF_2CF_2$— units was 66.2 mol %. The molecular weight per one —$SO_2F$ group of this polymer was 554. Further, the molecular weight of this polymer was measured by means of GPC (developing solvent: R-225cb, standard sample: methyl polymethacrylate), whereby the weight average molecular weight was 310,000, and the number average molecular weight was 180,000.

The softening temperature of a dried film obtained by the measurement of the dynamic viscoelasticity of the film obtained by the same method as in Example 6 except that this polymer was employed, was 148° C., and the specific resistivity of this film was 5.3 Ω·cm.

Example 8

Into an autoclave (internal capacity: 30 mL), 7.2 g of the compound (p2), 10.2 g of R-225cb and 8.7 mg of AIBN were charged and freeze-deaerated. Then, the internal temperature of the autoclave was maintained at 70° C., and TFE was introduced until the internal pressure became 1.4 MPa while the interior of the autoclave was stirred. Then, TFE was continuously introduced under such a condition that the internal pressure was maintained to be 1.4 MPa, and a reaction was carried out for two hours.

Then, the autoclave was cooled, and the internal pressure was released, whereupon hexane was immediately introduced into the autoclave. The flocculated content in the autoclave was recovered, washed three times with hexane, and then vacuum-dried at 80° C. for 12 hours, to obtain 9.0 g of a polymer.

This polymer was processed into a film having a thickness of 100 μm by a hot pressing method. As a result of the measurement of the surface reflection IR of this film, an absorption at 1,470 cm$^{-1}$ attributable to —$SO_2F$ and an absorption at 1140 cm$^{-1}$ attributable to the CF structure forming a 1,3-dioxolane structure, were confirmed. As a result of comparison of the two absorptions with the absorptions confirmed by the polymer 1, the proportion of monomer units (P2) to the total monomer units in the polymer 4 was 18 mol %, and the proportion of —$CF_2CF_2$— units was 82 mol %.

Process 2 for Preparation of Membrane-Catalyst Layer Assembly

In the same manner as in the process 1 for preparation of membrane-catalyst layer assembly, a coating fluid B for preparing a cathode catalyst layer and a coating fluid C for preparing an anode catalyst layer were respectively prepared and respectively applied and dried on an ETFE substrate film to prepare a cathode catalyst layer and an anode catalyst layer.

Then, the polymer obtained in Example 5 was processed into a film having an average thickness of 55 μm by a hot pressing method and then treated in the same manner as in Example 5 to obtain an acid form film.

This film was sandwiched between the cathode catalyst layer and the anode catalyst layer and hot-pressed at 120° C. under 3 MPa for 2 minutes for bonding to obtain a membrane-catalyst layer assembly (electrode area: 25 cm$^2$).

Evaluation 2 of Cell Characteristics of Membrane-Electrode Assembly

A membrane-electrode assembly was prepared in the same manner as in evaluation 1 of cell characteristics of membrane-electrode assembly except that the membrane-catalyst layer assembly obtained in the above process 2 for preparation was employed, and the membrane-electrode assembly was assembled into a cell for power generation, whereupon gases were supplied in the same manner as in evaluation 1. Power generation was continuously carried out by maintaining the temperature in the cell at 120° C. and the current density at 0.2 A/cm$^2$, and as a result, the voltage was 0.73 V.

Evaluation of Durability of Membrane-Electrode Assembly

Example 9

Process 3 for Preparation of Membrane-Catalyst Layer Assembly

In the same manner as in the process 1 for preparation of membrane-catalyst layer assembly, a coating fluid B for preparing a cathode catalyst layer and a coating fluid C for preparing an anode catalyst layer were respectively prepared and respectively applied and dried on an ETFE substrate film to prepare a cathode catalyst layer and an anode catalyst layer.

The polymer obtained in Example 2 was hot-pressed to obtain a film having a thickness of 50 μm, and in the same manner as in Example 1, hydrolysis and treatment for conversion to an acid form were carried out to obtain a membrane having sulfonic acid groups. Then, 6.0 mg of cerium nitrate (Ce(NO$_3$)$_3$.6H$_2$O) was dissolved in 500 mL of distilled water so as to contain cerium ions (+3 valent) corresponding to 15 mol % of sulfonic acid groups of this membrane, and the above ion exchange membrane was immersed therein, followed by stirring at room temperature for 40 hours by means of a stirring bar to have some of sulfonic acid groups in the ion exchange membrane ion-exchanged by cerium ions. Here, the cerium nitrate aqueous solution before and after the immersion was analyzed by ion chromatography, whereby it was found that 15% of sulfonic acid groups in this ion exchange membrane was substituted by cerium. This membrane was sandwiched between the above cathode catalyst layer and the anode catalyst layer, followed by hot pressing at 120° C. under 3 MPa for two minutes to bond the catalyst layers to the membrane, whereupon the substrate film were peeled off to obtain a membrane-catalyst layer assembly having an electrode area of 25 cm$^2$.

Evaluation of Durability of Membrane-Electrode Assembly

A membrane-electrode assembly was prepared in the same manner as evaluation 1 of cell characteristics of membrane-electrode assembly except that the membrane-catalyst layer assembly obtained in the above process 3 was used, and assembled into a cell for power generation, whereupon the gases were supplied in the same manner as in evaluation 1. By setting the cell temperature at 120° C. and the current density to be 0.2 A/cm², the voltage was recorded. The initial cell voltage and the time until it dropped to 0.5 V are shown in Table 2.

Example 10

A membrane-electrode assembly was prepared in the same manner as in Example 9 except that the membrane having sulfonic acid groups was prepared by means of the polymer obtained in Example 5 instead of the polymer obtained in Example 2, and the evaluation was carried out in the same manner as in Example 9. The results are shown in Table 2.

Example 11

A membrane-electrode assembly was prepared in the same manner as in Example 9 except that in Example 9, the membrane having sulfonic acid groups made of the polymer obtained in Example 2, was used as it is without treatment with the cerium nitrate aqueous solution, and the evaluation was carried out in the same manner as in Example 9. The results are shown in Table 2.

Example 12

In Example 10, a membrane-electrode assembly was prepared in the same manner as in Example 9 except that, the membrane having sulfonic acid groups made of the polymer obtained in Example 5, was used as it is without treatment with the cerium nitrate aqueous solution, and the evaluation was carried out in the same manner as in Example 9. The results are shown in Table 2.

TABLE 2

| | Polymer constituting the membrane | Incorporation of Ce | Initial output voltage (V) | Time until the voltage decreased to 0.5 V (hr) |
|---|---|---|---|---|
| Ex. 9 | Ex. 2 | Yes | 0.69 | 2,500 |
| Ex. 10 | Ex. 5 | Yes | 0.70 | 500 |
| Ex. 11 | Ex. 2 | No | 0.73 | 70 |
| Ex. 12 | Ex. 5 | No | 0.75 | 200 |

From Table 2, it is evident that the durability of the membrane-electrode assembly is improved by subjecting the electrolyte material for a polymer electrolyte fuel cell of the present invention to ion exchange with cerium ions.

INDUSTRIAL APPLICABILITY

The electrolyte material for polymer electrolyte fuel cells of the present invention has a high softening temperature as compared with the conventional material, and a polymer electrolyte fuel cell provided with such an electrolyte material can be operated at a temperature higher than the conventional one. As a result, it is able to contribute to high output or improvement in the cooling efficiency of the fuel cell.

The entire disclosures of Japanese Patent Application No. 2004-109869 filed on Apr. 2, 2004, Japanese Patent Application No. 2004-319086 filed on Oct. 26, 2004 and Japanese Patent Application No. 2004-311191 filed on Nov. 2, 2004 including specifications, claims, drawings and summaries are incorporated herein by reference in their entireties.

What is claimed is:

1. An electrolyte material for polymer electrolyte fuel cells, which is made of a polymer containing repeating units based on a fluoromonomer having a radical polymerization reactivity, wherein the repeating units contain a 5-membered ring, of which at least one carbon atom is contained in the main chain of the polymer, and an ionic group which is bonded to the 5-membered ring directly or via a perfluoroalkylene group having a linear or branched structure; the ionic group is represented by the formula $—(SO_2X(SO_2R^f)_g)^-H^+$, wherein $R^f$ is a linear or branched perfluoroalkyl group, and X is an oxygen atom, a nitrogen atom or a carbon atom, provided that when X is an oxygen atom, $g=0$, when X is a nitrogen atom, $g=1$, and when X is a carbon atom, $g=2$; and the polymer has a softening temperature of at least 120° C.

2. The electrolyte material for polymer electrolyte fuel cells according to claim 1, wherein the polymer is a perfluoropolymer.

3. The electrolyte material for polymer electrolyte fuel cells according to claim 1, wherein the polymer is a copolymer containing repeating units based on tetrafluoroethylene.

4. The electrolyte material for polymer electrolyte fuel cells according to claim 3, wherein the 5-membered ring is a 1,3-dioxolane ring.

5. The electrolyte material for polymer electrolyte fuel cells according to claim 3, wherein
the repeating units based on a fluoromonomer containing a 5-membered ring, are represented by the formula (A):

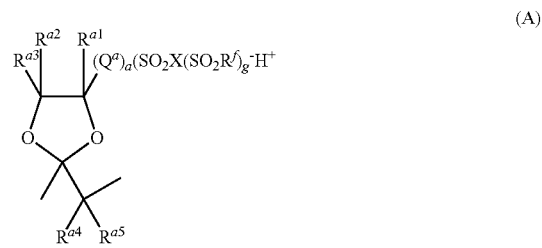

(A)

wherein $Q^a$ is a $C_{1-6}$ perfluoroalkylene group having a linear or branched structure, each of $R^{a1}$ to $R^{a5}$ which are independent of one another, is a perfluoroalkyl group or a fluorine atom, a is 0 or 1, $R^f$ is a linear or branched perfluoroalkyl group, and X is an oxygen atom, a nitrogen atom or a carbon atom, provided that when X is an oxygen atom, $g=0$, when X is a nitrogen atom, $g=1$, and when X is a carbon atom, $g=2$.

6. The electrolyte material for polymer electrolyte fuel cells according to claim 5, wherein in the formula (A), each of $R^{a4}$ and $R^{a5}$ is a fluorine atom.

7. The electrolyte material for polymer electrolyte fuel cells according to claim 5, wherein $R^f$ is a linear or branched perfluoroalkyl group containing an etheric oxygen atom.

8. The electrolyte material for polymer electrolyte fuel cells according to claim 5, wherein the perfluoroalkylene group is of formula $—(CF_2)_m—$ wherein m is from 1 to 6.

9. The electrolyte material for polymer electrolyte fuel cells according to claim 1, wherein the 5-membered ring is a 1,3-dioxolane ring.

10. The electrolyte material for polymer electrolyte fuel cells according to claim 1, wherein
the repeating units based on a fluoromonomer containing a 5-membered ring, are represented by the formula (A):

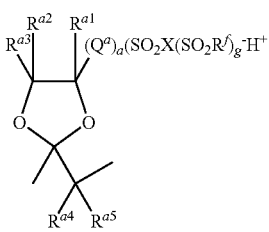

(A)

wherein $Q^a$ is a $C_{1-6}$ perfluoroalkylene group having a linear or branched structure, each of $R^{a1}$ to $R^{a5}$ which are independent of one another, is a perfluoroalkyl group or a fluorine atom, a is 0 or 1, $R^f$ is a linear or branched perfluoroalkyl group, and X is an oxygen atom, a nitrogen atom or a carbon atom, provided that when X is an oxygen atom, g=0, when X is a nitrogen atom, g=1, and when X is a carbon atom, g=2.

11. The electrolyte material for polymer electrolyte fuel cells according to claim 10, wherein in the formula (A), each of $R^{a4}$ and $R^{a5}$ is a fluorine atom.

12. The electrolyte material for polymer electrolyte fuel cells according to claim 10, wherein
the difference $\Delta T = T_2 - T_1$ where $T_2$ is the temperature at which the storage modulus becomes $1 \times 10^6$ Pa, and $T_1$ is the peak temperature of the loss modulus, obtainable by measurement of the dynamic viscoelasticity of the polymer, is from 40 to 150° C.

13. A membrane-electrode assembly for polymer electrolyte fuel cells, which comprises a cathode and an anode each having a catalyst layer containing a catalyst and a polymer electrolyte, and a polymer electrolyte membrane interposed between the cathode and the anode, wherein the polymer electrolyte contained in at least one of the catalyst layers of the cathode and the anode, is the electrolyte material as defined in claim 10.

14. The electrolyte material for polymer electrolyte fuel cells according to claim 10, wherein $R^f$ is a linear or branched perfluoroalkyl group containing an etheric oxygen atom.

15. The electrolyte material for polymer electrolyte fuel cells according to claim 10, wherein the perfluoroalkylene group is of formula —$(CF_2)_m$— wherein m is from 1 to 6.

16. The electrolyte material for polymer electrolyte fuel cells according to claim 1, wherein
the repeating units based on a fluoromonomer containing a 5-membered ring, are represented by the formula (B):

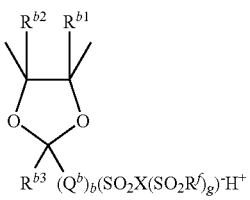

(B)

wherein $Q^b$ is a $C_{1-6}$ perfluoroalkylene group having a linear or branched structure, each of $R^{b1}$ to $R^{b3}$ which are independent of one another, is a perfluoroalkyl group or a fluorine atom, b is 0 or 1, $R^f$ is a linear or branched perfluoroalkyl group, and X is an oxygen atom, a nitrogen atom or a carbon atom, provided that when X is an oxygen atom, g=0, when X is a nitrogen atom, g=1, and when X is a carbon atom, g=2.

17. The electrolyte material for polymer electrolyte fuel cells according to claim 16, wherein in the formula (B), each of $R^{b1}$ and $R^{b2}$ is a fluorine atom.

18. The electrolyte material for polymer electrolyte fuel cells according to claim 17, wherein
the repeating units based on a fluoromonomer containing a 5-membered ring, are represented by the formula (B):

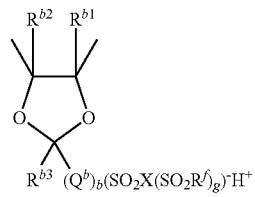

(B)

wherein $Q^b$ is a $C_{1-6}$ perfluoroalkylene group having a linear or branched structure, each of $R^{b1}$ to $R^{b3}$ which are independent of one another, is a perfluoroalkyl group or a fluorine atom, b is 0 or 1, $R^f$ is a linear or branched perfluoroalkyl group, and X is an oxygen atom, a nitrogen atom or a carbon atom, provided that when X is an oxygen atom, g=0, when X is a nitrogen atom, g=1, and when X is a carbon atom, g=2.

19. The electrolyte material for polymer electrolyte fuel cells according to claim 18, wherein the repeating units based on the fluoromonomer contain a 5-membered ring containing one or two carbon atoms.

20. The electrolyte material for polymer electrolyte fuel cells according to claim 18, wherein in the formula (B), each of $R^{b1}$ and $R^{b2}$ is a fluorine atom.

21. A membrane-electrode assembly for polymer electrolyte fuel cells, which comprises a cathode and an anode each having a catalyst layer containing a catalyst and a polymer electrolyte, and a polymer electrolyte membrane interposed between the cathode and the anode, wherein the polymer electrolyte contained in at least one of the catalyst layers of the cathode and the anode, is the electrolyte material as defined in claim 16.

22. The electrolyte material for polymer electrolyte fuel cells according to claim 18, wherein the perfluoroalkylene group is of formula —$(CF_2)_m$— wherein m is from 1 to 6.

23. The electrolyte material for polymer electrolyte fuel cells according to claim 16, wherein
the difference $\Delta T = T_2 - T_1$ where $T_2$ is the temperature at which the storage modulus becomes $1 \times 10^6$ Pa, and $T_1$ is the peak temperature of the loss modulus, obtainable by measurement of the dynamic viscoelasticity of the polymer, is from 40 to 150° C.

24. The electrolyte material for polymer electrolyte fuel cells according to claim 16, wherein $R^f$ is a linear or branched perfluoroalkyl group containing an etheric oxygen atom.

25. The electrolyte material for polymer electrolyte fuel cells according to claim 16, wherein the perfluoroalkylene group is of formula —$(CF_2)_m$— wherein m is from 1 to 6.

26. The electrolyte material for polymer electrolyte fuel cells according to claim 1, wherein the repeating units based on a fluoromonomer containing a 5-membered ring, are contained in an amount of from 5 to 50 mol % of the total repeating units in the polymer.

27. The electrolyte material for polymer electrolyte fuel cells according to claim 1, wherein the difference $\Delta T = T_2 - T_1$ where $T_2$ is the temperature at which the storage modulus becomes $1 \times 10^6$ Pa, and $T_1$ is the peak temperature of the loss modulus, obtainable by measurement of the dynamic viscoelasticity of the polymer, is from 40 to 150° C.

28. An electrolyte membrane for polymer electrolyte fuel cells, made of the electrolyte material as defined in claim 1.

29. The electrolyte membrane for polymer electrolyte fuel cells according to claim 28, which contains at least one type of atoms selected from the group consisting of cerium and manganese.

30. The electrolyte membrane for polymer electrolyte fuel cells according to claim 29, which contains at least one type selected from the group consisting of cerium ions and manganese ions.

31. A membrane-electrode assembly for polymer electrolyte fuel cells, which comprises a cathode and an anode each having a catalyst layer containing a catalyst and a polymer electrolyte, and a polymer electrolyte membrane interposed between the cathode and the anode, wherein the polymer electrolyte membrane is the electrolyte membrane as defined in claim 28.

32. The electrolyte material for polymer electrolyte fuel cells according to claim 1, wherein the repeating units based on the fluoromonomer contain a 5-membered ring containing one or two carbon atoms.

33. The electrolyte material for polymer electrolyte fuel cells according to claim 1, wherein $R^f$ is a linear or branched perfluoroalkyl group containing an etheric oxygen atom.

34. The electrolyte material for polymer electrolyte fuel cells according to claim 1, wherein the perfluoroalkylene group is of formula $—(CF_2)_m—$ wherein m is from 1 to 6.

35. A process for producing an electrolyte material for polymer electrolyte fuel cells, as defined in claim 1, which comprises subjecting a fluoromonomer having a 5-membered ring, a carbon-carbon double bond, of which at least one of the carbon atoms is included in the 5-membered ring, and a fluorosulfonyl group which is bonded to the 5-membered ring directly or via a perfluoroalkylene group having a linear or branched structure, to radical polymerization in the presence of a radical initiating source, and then converting the fluorosulfonyl group to an ionic group represented by the formula $—(SO_2X(SO_2R^f)_g)^-H^+$, wherein $R^f$ is a linear or branched perfluoroalkyl group, and X is an oxygen atom, a nitrogen atom or a carbon atom, provided that when X is an oxygen atom, g=0, when X is a nitrogen atom, g=1, and when X is a carbon atom, g=2.

36. The process for producing an electrolyte material for polymer electrolyte fuel cells according to claim 35, wherein the fluoromonomer has a 5-membered ring having one or two oxygen atoms.

37. The process for producing an electrolyte material for polymer electrolyte fuel cells according to claim 35, wherein $R^f$ is a linear or branched perfluoroalkyl group containing an etheric oxygen atom.

38. The process for producing an electrolyte material for polymer electrolyte fuel cells according to claim 35, wherein the perfluoroalkylene group is of formula $—(CF_2)_m—$ wherein m is from 1 to 6.

* * * * *